(12) United States Patent
Silverman

(10) Patent No.: US 8,961,932 B2
(45) Date of Patent: Feb. 24, 2015

US008961932B2

(54) "MICRO-PATCH" FOR ASSESSMENT OF THE LOCAL MICROVASCULATURE AND MICROCIRCULATORY VASOREACTIVITY

(76) Inventor: David G. Silverman, West Redding, CT (US)

( * ) Notice: Subject to any disclaimer, the term of this patent is extended or adjusted under 35 U.S.C. 154(b) by 1524 days.

(21) Appl. No.: 12/059,383

(22) Filed: Mar. 31, 2008

(65) Prior Publication Data

US 2008/0241199 A1    Oct. 2, 2008

Related U.S. Application Data

(60) Provisional application No. 60/920,823, filed on Mar. 30, 2007.

(51) Int. Cl.
*A61K 51/00* (2006.01)
*A61K 31/04* (2006.01)
*A61B 5/026* (2006.01)
*A61K 31/221* (2006.01)
*A61B 5/00* (2006.01)

(52) U.S. Cl.
CPC .............. *A61K 31/04* (2013.01); *A61B 5/0261* (2013.01); *A61K 31/221* (2013.01); *A61B 5/726* (2013.01)
USPC ........................................................ 424/9.1

(58) Field of Classification Search
USPC ........................................................ 424/9.1
See application file for complete search history.

(56) References Cited

U.S. PATENT DOCUMENTS

| | | | | |
|---|---|---|---|---|
| 5,466,465 | A * | 11/1995 | Royds et al. | 424/449 |
| 6,417,205 | B1 * | 7/2002 | Cooke et al. | 514/343 |
| 6,656,147 | B1 * | 12/2003 | Gertsek et al. | 604/28 |
| 6,741,895 | B1 * | 5/2004 | Gafni et al. | 607/138 |
| 2005/0249774 | A1 * | 11/2005 | Pauletti et al. | 424/423 |

OTHER PUBLICATIONS

Bjarnason and Fischer. Contact Dermatitis. Sep. 1998;39(3):112-8.*
Scheindlin. Molecular Interventions. Dec. 2004;4(6):308-312.*
Saez et al. Br J Clin Pharmacol. 2005 59(5):511-19.*
Suzuki (Stroke. 1993;24:1049-1053).*
Kaski (Circulation 74, No. 6, 1255-1265, 1986).*
Benjamin (Hypertension. 1995; 25: 918-923).*
"Demise of a Blockbuster Drug Complicates Pfizer's Revamp", Wall Street Journal, Dec. 4, 2006.
Opazo Saez, A.M., et al., "Laser Doppler Imager (LDI) Scanner and Intradermal Injection for InVivo . . . ", British Journal of Clinical Pharmacology, May 2005, 59(5):511-519.
Schonberger, R.B., et al., "Topical Non-Iontophoretic Application of Acetylcholine and Nitroglycerin . . . ", Yale J Biol Med, 2006, 78:229-235.
Silverman, D.G., et al., "Detection and Characterization of Cholinergic Oscillatory Control in the Forehead Microvasculature . . . ", Microvasc Res, 2001, 61:144-7.
Silverman, D.G., et al., "Distinction Between Aropine-Sensitive Control of Microvascular and Cardiac Oscillatory Activity", Microvasc Res, 2002, 63:196-208.
Wardell, K., et al., "Spatial Heterogeneity in Normal Skin Perfusion Recorded with Laser Doppler Imaging and Flowmetry", Microvascular Research, Jul. 1994, 48(1):26-38.
Anderson, T.J., et al., "Close Relation of Endothelial Function in the Human Coronary and Peripheral Circulations", JACC, 1995, 26(5): 1235-1241.
Anderson, T.J., et al., "A Comparative Study of Four Anti-Hypertensive Agents on Endothelial Function in Patients with Coronary Disease", J Am Coll Cardiol 1998, 31:327A, Abst.
Anderson, T.J., et al., "Systemic Nature of Endothelial Dysfunction in Atherosclerosis", Am J Cardiol, 1995, 75:71B.
Anderson, T.J., et al., "The Effect of Cholesterol-Lowering and Antioxidant Therapy on Endothelium-Dependent Coronary Vasomotion". N Engl J Med 1995, 332:488.
Bossaller, C., et al., "Impaired Muscarinic Endothelium-Dependent Relaxation and Cyclic Guanosine 5'-Monophosphate . . . ", Journal of Clinical Investigation, 1987, 79:170-4.
Braverman, I.M, et al., "Topographic Mapping of the Cutaneous Microcirculation Using Two Outputs of Laser-Doppler Flowmetry . . . "Microvascular Research, Jul. 1992, 44(1):33-48.
Christen, S, et al., "Dose-Dependent Vasodilatory Effects of Acetylcholine and Local Warming on Skin Microcirculation", Journal of Cardiovascular Pharmacology, 2004, 44:659-64.
Drexler, H., Zeiher, A.M., Progression of Coronary Endothelial Dysfunction in man and its Potential Clinical Significance, Basic Research in Cardiology. 1991, 2:223-32.
Droog, E.J., Sjoberg, F., "Nonspecific Vasodilatation During Transdermal Iontophoresis—the Effect of Voltage Over the Skin", Microvascular Research, 2003, 65:172-8.
Ferrell, W.R., et al., "Elimination of Electrically Induced Iontophoretic Artefacts: Implications for Non-Invasive . . . ", Journal of Vascular Research, 2002, 39:447-55.
Furchgott, R.F., Zawadzki, J.V., "The Obligatory Role of Endothelial Cells in the Relaxation of Arterial Smooth Muscle by Acetylcholine", Nature, 1980, 288: 373-6.
Holowatz, L.A., et al., "Mechanisms of Acetylcholine-Mediated Vasodilatation in Young and Aged Human Skin", Journal of Physiology, 2005, 563:965-73.
Khan, F., et al., "Influence of Vehicle Resistance on Transdermal Iontophoretic Delivery of Acetylcholine and Sodium . . . ", Journal of Applied Physiology, 2004, 97:883-7.

(Continued)

*Primary Examiner* — David J Blanchard
*Assistant Examiner* — Devang Thakor
(74) *Attorney, Agent, or Firm* — Welsh Flaxman & Gitler LLC

(57) ABSTRACT

A method for interrogating the microcirculation of a subject for use in characterizing function in health and disease, monitor changes in microcirculation over time, and identify responses in microcirculation to potentially harmful or beneficial interventions. The method includes delivering a study agent to a study surface for trans-surface delivery to the microvasculature of the subject and monitoring the microvasculature of the subject in the area of the study surface. A system is also provided which includes a micro-patch for delivery of study agent to a study surface for trans-surface delivery to the microvasculature of the subject and a monitoring probe for monitoring the microvasculature of the subject in the area of the study surface.

26 Claims, 27 Drawing Sheets

(56) References Cited

OTHER PUBLICATIONS

Ledger, P., "Skin Biological Issues in Electrically Enhanced Transdermal Delivery", Advanced Drug Delivery Reviews. 1991, 9:289-307.

Mo, C., Stout, R.G., Shelley, K.H., Tantawy, H., Silverman, D.G., Acute Microcirculatory Effects of Nicotine in Non-Smoking Volunteers, Anesthesiology 2004, 101:A246.

Morris, S.J., Shore, A.C., Tooke, J.E., "Responses of the Skin Microcirculation to Acetylcholine and Sodium Nitroprusside in Patients with NIDDM", Diabetologia, 1337:38-44.

Nissen, A.,et al., "Consistency of Laser Doppler Assessments of Vasoreactivity", American Society of Anesthesiologists, 2006, 2A244.

Nissen, A.F., et al., "Sensitivity of Acetylcholine and Nitroglycerin-Induced Vasodilation to Endothelial Impairment", Anesthesiology, 2007, 107:A291.

Noon, J.P., et al., "Studies with Iontophoretic Administration of Drugs to Human Dermal Vessels in Vivo: Cholinergic . . . ", Br J Clin Pharmacol, 1998, 45:545-50.

Peters, E.J., et al., "The Benefit of Electrical Stimulation to Enhance Perfusion in Persons with Diabetes Mellitus", Journal of Foot & Ankle Surgery, 1998, 37:396-400.

Thanyasiri, P, et al., "Endothelial Dysfunction Occurs in Peripheral Circulation of Patients with . . . ", American Journal of Physiology Heart & Circulatory Physiology, 2005, 289.

Wang, S., Omar, W., Awad, A., Scannell, M., Silverman, D.G., "Direct and Reflexive Autonomic Effects of Acupuncture in Healthy Subjects", Int Anesth Res Soc, 2002, S-215.

Wilkin, J.K., "Poiseuille, Periodicity, and Perfusion: Rhythmic Oscillatory Vasomotion in the Skin", The Journal of Investigative Dermatology, Aug. 1989, 93(2): 113S-118S.

Yoshida, M., et al.,"Impaired Forearm Vasodilatation by Acetylcholine in Patients with Hypertension", Heart & Vessels, 1991, 6:218-23.

\* cited by examiner

"MICRO-PATCH" FOR ASSESSMENT OF THE LOCAL MICROVASCULATURE AND MICROCIRCULATORY VASOREACTIVITY

CROSS REFERENCE TO RELATED APPLICATION

This application claims the benefit of U.S. Provisional Patent Application Ser. No. 60/920,823, filed Mar. 30, 2007, entitled "'Micro-Patch' for Assessment of the Local Microvasculature and Microcirculatory Vasoreactivity".

BACKGROUND OF THE INVENTION

1. Field of the Invention

The invention relates to a system(s), method(s) and apparatus(es) for assessment of local microvasculature and microcirculatory vasoreactivity.

2. Description of the Related Art

Multiple studies have indicated that assessment of the microvasculature in an accessible area not only delineates the status of the local microvasculature at that site but also correlates with vascular injury throughout the body, including the heart. [Anderson T J: Assessment of endothelial function: research tool or clinical reality? Cardiology Review: Endothelial Function Forum CME, July 1999; Anderson T J, Meredith I T, Yeung A C, et al. The effect of cholesterol-lowering and antioxidant therapy on endothelium-dependent coronary vasomotion. N Engl J Med 1995; 332:488; Anderson T J, Overhiser R W, Haber H, Charbonneau F. A comparative study of four anti-hypertensive agents on endothelial function in patients with coronary disease. J Am Coll Cardiol 1998; 31:327A, Abstract #1147 54.]However, the ability to interrogate local microvasculature in a safe, noninvasive, nonintrusive manner has been limited.

Prior to the development of the current invention, assessments of the effects of drugs and alternative agents (herein referred to interchangeably as "drugs", "agents" or "study agents" at the level of the microvasculature (e.g., arterioles, capillaries, venules) were performed primarily in in vitro tissue baths, after systemic drug administration (intravenous, intramuscular, oral), or after driving drug through the skin with electric current.

In vitro testing of vasoactive drugs typically entails exposure of tissue to different concentrations of an agent (or alternative stimulus) by direct application or by immersion in a drug-containing bath. Such testing led to the discovery in the early 1980's of the importance of the microvasculature and the endothelium lining its vessels; Acetylcholine, a prominent neurotransmitter, causes vasodilation of blood vessels with an intact inner endothelial lining and vasoconstriction of vessels with damaged or missing endothelial lining. [Furchgott R F, Zawadzki J V. The obligatory role of endothelial cells in the relaxation of arterial smooth muscle by acetylcholine. Nature. 1980; 288:373-6.] While valuable for initial characterization of drug effect, this method is not readily applicable in intact humans and does not necessarily reflect what would happen in an intact preparation; i.e., the findings may not readily transfer to clinical settings. These limitations have prompted in vivo studies in healthy volunteers and patients.

The evaluation in intact humans primarily has been accomplished by systemic administration of a drug (e.g., by a pill, lozenge, solution, or systemic intravenous or intramuscular administration). Systemic administration typically generates direct and indirect responses throughout the body; i.e., at the level of the heart, arteries, arterioles, capillaries, venules and veins. Delineation of effects at the level of the microvasculature is limited by a variety of factors, including:

difficulty obtaining/titrating tissue levels;
difficulty comparing active and placebo effects concurrently;
activation of multiple systemic responses and reflexes which may modulate the effect at the target site;
the potential for unwanted/dangerous systemic effects and side effects, thereby making testing impractical or impossible. For example, the inventor and his colleagues have shown that testing the effects of nicotine on the microvasculature entailed the use of systemic doses (e.g., via lozenges) that resulted in pronounced changes in systemic blood pressure and heart rate that necessitated stopping the study in some subjects. [Mo C, Stout R G, Shelley K H, Tantawy H, Silverman D G: Acute microcirculatory effects of nicotine in non-smoking volunteers. Anesthesiology 2004; 101:A246.]. Likewise, to test the systemic effects of a vasoconstricting drug such as phenylephrine [Silverman D G, Stout R G: Distinction between atropine-sensitive control of microvascular and cardiac oscillatory activity. Microvasc Res 63:196-208, 2002], one may need to deliver doses of drug which can potentially cause significant systemic vasoconstriction and hypertension.

To overcome the aforementioned limitations associated with systemic administration of a drug, investigators have employed selective intravascular injection into a regional artery or vein. Despite the undesirable features of this approach as summarized below, the perceived importance of determining the reactivity of the in different disorders has prompted clinicians and investigators to administer pharmacologic agents such as acetylcholine into coronary (heart) as well as brachial (arm) and femoral (leg) arteries. In the context of atherosclerotic disease, intracoronary injection of acetylcholine is associated with impaired vasodilation or frank vasoconstriction, leading to the suggestion that it serve as a test for early detection of coronary artery disease. Prexler H, Zeiher A M. Progression of coronary endothelial dysfunction in man and its potential clinical significance. *Basic Research In Cardiology.* 1991; 2:223-32., Bossaller C, Habib G B, Yamamoto H, Williams C, Wells S, Henry P D. Impaired muscarinic endothelium-dependent relaxation and cyclic guanosine 5'-monophosphate formation in atherosclerotic human coronary artery and rabbit aorta. *Journal of Clinical Investigation.* 1987; 79:170-4; and Thanyasiri P, Celermajer D S, Adams M R. Endothelial dysfunction occurs in peripheral circulation patients with acute and stable coronary artery disease. *American Journal of Physiology Heart & Circulatory Physiology.* 2005; 289.] Likewise, the vasodilatory response to brachial or femoral artery injection of acetylcholine is compromised in the presence of coronary artery disease. [Yoshida M, Imaizumi T, Ando S, Hirooka Y, Harada S, Takeshita A. Impaired forearm vasodilatation by acetylcholine in patients with hypertension. *Heart & Vessels.* 1991; 6:218-23] and hypertension. However, the need for an intra-arterial injection has led to such invasive tests being confined primarily to research settings.

Potential limitations of such regional injection include:
Invasiveness of injection.
Discomfort associated with injection and hence pain-related responses.
Regional pressure and volume changes as a consequence of injections.
The need to apply tourniquets to the regions and/or physically alter blood flow in an alternative manner.
Leakage to the other regions.

Hence, such testing primarily has been confined to research settings.

In an effort to avoid the invasive nature of such injections, investigators have sought other means of delivery. However, the techniques recommended heretofore have significant shortcomings. Most notably, local injection of drug at the planned site of monitoring can be painful and may produce unreliable results because of local tissue damage and irritation, as well as potential disturbance of tissue planes, thereby leading to inconsistent spread of drug. [Opazo Saez A M. Mosel F. Nurnberger J. Rushentsova U. Gossl M. Mitchell A. Schafers R F. Philipp T. Wenzel R R. Laser Doppler imager (LDI) scanner and intradermal injection for in vivo pharmacology in human skin microcirculation: responses to acetylcholine, endothelin-1 and their repeatability. British Journal of Clinical Pharmacology 59(5):511-519, 2005 May.]

This has led to the use of a needleless technique such as iontophoresis, wherein an electrical current drives drug through the skin. As discussed below in greater detail, there are iontophoretic devices that indeed have the ability for drug delivery as well as for laser Doppler monitoring of local blood flow. Such monitoring in the context of iontophoresis has quantified vasodilation at selected sites in response to iontophoretic application of acetylcholine in healthy subjects, and has documented that this response is compromised in patients with diabetes. However, iontophoresis is irritating to the tissue, such that the process itself alters microvascular function and microcirculatory flow; and iontophoretic delivery of inactive vehicle causes changes.

While one could wait several minutes after iontophoresis to allow for the effects of electrical current to abate, this also would allow time for the drug to redistribute and potentially leave the local area, especially if the drug has a vasodilatory effect which would increase its uptake by the circulation. Overall, factors limiting the widespread use of iontophoresis in the clinical setting include:

1) it can be painful (this not only would be undesirable for the subject but also might cause pain-induced changes in systemic blood flow);
2) the device requires a well or pad for the drug and is relatively bulky and thus is not necessarily well-suited for placement on small sites such as digits and also on sites that are not perfectly level; Moreover, these components may impede monitoring at portions of the delivery/study sites;
3) dosage and time-course are dictated by the need to deliver drug with an electric current;
4) if one has to check periodically to see the effect of iontophoretic delivery on local perfusion while allowing for the direct effect of the electrical stimulation to abate, this could lead to a time-consuming evaluation and undesirable probe repositioning;
5) the vehicle alone (without active drug) can cause changes in local perfusion;
6) iontophoresis can cause an electrical burn under the pad; and
7) electric current itself has been shown to be a potent vasodilator; even when data are modified to account for a potential current-induced effect, the current remains a potential confounder in such studies; its effect varies among specific vehicles and drugs as well as spatially over the area of drug delivery.

The limitation as well as the potential benefits of iontophoresis in the context of disease have been studied extensively. [Christen S, Delachaux A, Dischl B, Golay S, Liaudet L, Feihl F, Waeber B. Dose-dependent vasodilatory effects of acetylcholine and local warming on skin microcirculation. *Journal of Cardiovascular Pharmacology.* 2004; 44:659-64. Noon J P, Walker B R, Hand M F, Webb D J: Studies with iontophoretic administration of drugs to human dermal vessels in vivo: cholinergic vasodilatation is mediated by dilator prostanoids rather than nitric oxide. Br J Clin Pharmacol 1998; 45:545-50; Wang S, Omar W, Awad A, Scannell M, Silverman D G: Direct and reflexive autonomic effects of acupuncture in healthy subjects. Int Anesth Res Soc S-215, 2002; Morris S J, Shore A C, Tooke J E. Responses of the skin microcirculation to acetylcholine and sodium nitroprusside in patients with NIDDM. *Diabetologia.* 1337; 38:1337-44. Ledger P. Skin biological issues in electrically enhanced transdermal delivery. *Advanced Drug Delivery Reviews.* 1991; 9:289-307), Peters E J, Armstrong D G, Wunderlich R P, Bosma J, Stacpoole-Shea S, Lavery L A. The benefit of electrical stimulation to enhance perfusion in persons with diabetes mellitus. *Journal of Foot & Ankle Surgery.* 1998; 37:396-400.; Ferrell W R, Ramsay J E, Brooks N, Lockhart J C, Dickson S, McNeece G M, Greer I A, Sattar N. Elimination of electrically induced iontophoretic artefacts: implications for non-invasive assessment of peripheral microvascular function. *Journal of Vascular Research.* 2002; 39:447-55.; Droog E J, Sjoberg F. Nonspecific vasodilatation during transdermal iontophoresis—the effect of voltage over the skin. *Microvascular Research.* 2003; 65:172-8.; Khan F, Newton D J, Smyth E C, Belch J J. Influence of vehicle resistance on transdermal iontophoretic delivery of acetylcholine and sodium nitroprusside in humans. *Journal of Applied Physiology.* 2004; 97:883-7.; Mar and Holowatz L A, Thompson C S, Minson C T, Kenney W L. Mechanisms of acetylcholine-mediated vasodilatation in young and aged human skin. *Journal of Physiology.* 2005; 563:965-73].

Transdermal Drug Delivery:

The prior art includes transdermal applicants (e.g., gels, creams, ointments that are secured to a supporting substrate or backing)—herein referred to as "patches" because they commonly are supplied in the form of a patch—for a variety of purposes that transdermally deliver drugs in a non-iontopheretic manner (i.e., transdermal (or trans-surface) delivery without the use of electrical energy). However, these patches have limitations due to restricted size and restricted dose. Various patches have been used in the delivery of systemically effective plasma concentrations of a variety of drugs, including:

fentanyl patch for delivery of systemic levels of the analgesic opioid fentanyl, in order to achieve systemic levels commensurate with those by intravenous injection;

scopolamine patch to achieve systemic levels of scopolamine for the treatment of nausea;

nicotine patch to provide systemic levels of nicotine in individuals hoping to wean from cigarettes without symptoms of nicotine withdrawal;

nitroglycerin patch to achieve systemic levels of the cardiac medicine nitroglycerin;

clonidine patch to achieve systemic levels of this antihypertensive medication; and estrogen patch to deliver systemic levels of this hormone.

As noted above, each of the aforementioned patches is designed to deliver a systemic level of drug and thus, in its current form, is not suitable for the goals of strictly local assessment of the microvasculature. If one of these "systemic patches" were to be used for the purpose of assessing the effect of the drug, it would be plagued with most of the limitations and systemic side effects associated with oral or intravenous administration—e.g., remote effects, systemic effects.

Prior patch preparations have been designed to achieve a local effect (e.g., to treat local pain, itching, etc.). These include ointments, many of which are in the form of patches:

Lidocaine ointment/patch—delivers lidocaine to a painful site under the patch in the hope of achieving local pain relief.

Tiger Balm® ointment/patch (for local muscle pain).

TheraPatch® (with calamine to treat local itching).

EMLA cream: eutectic mixture of the local anesthetics lidocaine and prilocaine (which is used to provide analgesia in children prior to needle insertion).

Prior preparations used to achieve a local vascular effect include:

Phenylephrine nose spray to achieve vasoconstriction of nasal mucosa.

Nitroglycerin ointment and l-arginine ointment to increase local blood flow and thereby improve local healing (based on known vasodilating properties of the drug).

To the best of the inventor's knowledge, none of these patches has been introduced or utilized for the diagnosis and assessment of vascular disorders. In addition, except for the local effect of EMLA ("eutectic mixture of local anesthetics"), they are designed to cause changes to a relatively large area; e.g., 5×5 cm size as opposed to customized limited doses. This can result in significant systemic levels of the drug and thus their use for the assessment of changes in the microvasculature would be compromised. Furthermore, the widespread local delivery will affect much more than the local microvasculature and may encompass multiple vascular beds, including larger arteries and veins. An additional problem of a large delivery area is that it may promote "steal" among vessels in the region as each of the dilated vessels "competes" for increased blood flow.

Monitoring the Local Microvasculature:

As stated above, none of the preparations to date has been designed to include medications for the purpose of measuring microvascular responsiveness; nor have they been adapted for real-time monitoring while the patch is in place. They thus have not been adapted with any mechanism for assessing such flow and have not been accompanied by a placebo patch for the purpose of enabling effective double-blind investigations which isolate the effect of the drug itself as opposed to other variables such as placebo patch application and administration of the vehicle for drug delivery. Additionally, the preparations often are not designed for consistently optimum light transmission, with customization of agent concentration and vehicle color and consistency.

Although multiple mechanisms for assessing surface blood flow have been developed, none of these current mechanisms for assessing surface blood flow is ideally suited for monitoring the changes in perfusion induced by micro-patches in accordance with the present invention and as described below in greater detail. In particular, the shortcomings of the current mechanisms for assessing surface blood flow are as follows:

Thermometry may be more indicative of flow in large vessels than in a restricted microcirculatory bed; the small temperature change that may result from a local microvascular effect induced by a micro-patch is overshadowed by other changes. Furthermore, it is influenced by ambient temperature.

Angiography requires radiological contrast material and special detection equipment; moreover, it is relatively ineffective at delineating relatively small changes in the microvasculature.

Radioisotopes entail the use of radioactive material.

Capillaroscopy requires a relatively cumbersome microscope and is not suited to monitoring multiple sites.

Plethysmography primarily is reflective of volume changes in a region, as opposed to local microcirculatory changes.

Laser Doppler flowmetry, with a surface probe or via a scanning imager, and laser speckle analysis appear better suited for monitoring the microvasculature as developed in accordance with the present invention and as discussed below in the description of the present invention.

As stated above in the context of iontophoresis, the local microcirculation may be monitored with a light-transmitting technique such as laser Doppler flowmetry. This technique entails delivery of light of uniform wavelength to the tissue under study; this is scattered (phase-shifted) by moving red blood cells near the tissue surface, such that the degree of alteration is proportional to the concentration of moving blood cells and their velocity. As with any of the monitoring techniques that rely upon light transmission, laser Doppler flowmetry would be distorted by surface application of a nontransparent agent or vehicle as required by iontophoresis and/or their opaque carrying structures.

In its simplest form, laser Doppler flowmetry entails placements of a probe on a study site to gain an indication of blood. However, since a laser Doppler reading is influenced by the number and size of blood vessels under a probe (commonly between 20 and 50 capillaries in one to three arteriolar-capillary networks), the reading is relative. Therefore, the technique is primarily used for comparison among sites or to monitor changes at a given site during a systemic challenge (since the probe can remain at a single monitoring site without the need for removal and replacement). Without the inventive modifications as discussed below in describing the present invention, use of a standard laser Doppler probe with a standard drug patch is prone to error and distortion, most notably: a) most patches have an opaque background, thereby preventing light transmission to the study site; b) after baseline readings are obtained, the probe would need to be removed to enable patch placement—this leads to distortion as a consequence of spatial heterogeneity (as discussed below). The inventor and his colleagues have documented variability among sites within millimeters of each other. [Braverman I M. Schechner J S. Silverman D G. Keh-Yen A. Topographic mapping of the cutaneous microcirculation using two outputs of laser-Doppler flowmetry: flux and the concentration of moving blood cells. Microvascular Research 44(1):33-48, 1992 July].

The laser Doppler scanning imager scans multiple sites to provide an image of a broader region. However, since it monitors sites sequentially, it does so at the cost of decreased temporal resolution at a given site and hence has the potential for increased temporal artifact (as a consequence of changing conditions as well as subject movement).

The laser speckle imager overcomes the laser Doppler scanner's lack of temporal resolution by acquiring signals simultaneously on a multipixel charged couple device. However, it is not certain as to whether it can generate a successful signal/noise ratio and may not enable optimum sensitivity to gradations in flow; and the speckle pattern is very sensitive to surface irregularities as may result from drug and/or vehicle application; moreover, the degree of speckling may change with time as a cream or ointment is absorbed (even without changes in blood flow).

In view of the foregoing, a need exists for improved diagnostic testing systems, methods and apparatuses for integrated use in the assessment of microcirculation. The present invention provides such systems, methods and apparatuses.

SUMMARY OF THE INVENTION

It is, therefore, an object of the present invention to provide a mechanism of delivery of a vasoactive drug and monitoring its effect ideally so as to enable attainment of a baseline without having to move a laser Doppler flowmetry probe or alternative monitoring device, enable delivery of active drug with minimal impact by other factors that may distort readings of vasoreactivity (e.g., altered light transmission, reactions to local current or needle-induced injury), and enable delivery of an amount of drug that has little or no effect on a remote site and little or no systemic effects as may be confirmed by heart rate, heart rate variability and blood pressure. Ideally this is accomplished in accordance with the present invention by using a very small amount of a clear solution or other clear substrate in the form of what herein is referred to as a "micro-patch." If indicated, the lack of an effect on light transmission can be confirmed by or corrected for by placebo application, (i.e., a placebo micro-patch) at another site. This should have similar light transmission characteristics and other similar physical characteristics such as osmolality and pH.

It is also an object of the present invention to provide a method wherein the optimal site for monitoring within a given region (i.e., the site with the richest microvasculature) can be determined by moving the monitoring probe in very small increments. A method for doing this with the laser Doppler flowmetry probe—but without an accompanying micro-patch has already been described by the inventor's team [Braverman I M. Schechner J S. Silverman D G. Keh-Yen A. Topographic mapping of the cutaneous microcirculation using two outputs of laser-Doppler flowmetry: flux and the concentration of moving blood cells. Microvascular Research 44(1):33-48, 1992 July, which is incorporated herein by reference]. It should be noted, however, that the 10×10 cm mapping grid used in that investigation was not designed for unobtrusive assessment over a micro-patch and was used exclusively on a flat surface. In collaboration with others, the inventor [Wardell K. Braverman I M. Silverman D G. Nilsson G E. Spatial heterogeneity in normal skin perfusion recorded with laser Doppler imaging and flowmetry. Microvascular Research 48(1):26-38, 1994 July] has delineated spatial heterogeneity with a laser Doppler scanner (imager). Additionally, laser speckle imaging can provide scanning of multiple sites. The integration of such mapping technologies with micro-patch application are discussed below. In addition, the present invention introduces an assembly for micro-patch administration beneath an elevated monitoring probe.

It is also an object of the present invention to provide an application of a monitor other than traditional laser Doppler flowmetry, wherein, in accordance with an inventive means of trans-surface agent delivery, an alternative mechanism of assessment may entail laser Doppler scanning imager, laser speckle imaging, plethysmography, high-resolution thermometry or capillaroscopy.

It is also an object of the present invention to provide a method wherein the optimal site for monitoring within a given region (i.e., the site with the richest microvasculature) can be determined by moving the monitoring probe in very small increments. A method for doing this with the laser Doppler flowmetry probe has already been described by the inventor's team [Braverman I M. Schechner J S. Silverman D G. Keh-Yen A. Topographic mapping of the cutaneous microcirculation using two outputs of laser-Doppler flowmetry: flux and the concentration of moving blood cells. Microvascular Research 44(1):33-48, 1992 July, which is incorporated herein by reference]. It should be noted, however, that the 10×10 cm mapping grid used in that investigation was not designed for unobtrusive assessment over a micro-patch and was used exclusively on a flat surface. In collaboration with others, the inventor [Wardell K. Braverman I M. Silverman D G. Nilsson G E. Spatial heterogeneity in normal skin perfusion recorded with laser Doppler imaging and flowmetry. Microvascular Research 48(1):26-38, 1994 July] has delineated spatial heterogeneity with a laser Doppler scanner (imager). Additionally, laser speckle imaging can provide scanning of multiple sites. The integration of such mapping technologies with micro-patch application are discussed below. In addition, the present invention introduces an assembly for micro-patch administration beneath an elevated monitoring probe.

It is also an object of the present invention to provide for assessments of the effects of vasoactive drugs beneath the active micro-patch that can be determined independently or in comparison to a placebo micro-patch or reference site.

It is also an object of the present invention to provide for assessments of changes in flow that can be made strictly based upon the change in flow beneath the micro-patch as an isolated challenge or in the context of an additional challenge. Such challenges may include but are not limited to: topical administration of another drug at the same site; systemic administration of another drug or the same drug; and/or systemic challenge such as hyperventilation, cool water immersion of an extremity, or mental stress.

It is also an object of the present invention to provide for assessing increases or decreases in local blood flow via a technique such as laser Doppler flowmetry in a variety of ways, including: magnitude of the mean rise (DC component); change in the systolic and/or the diastolic values; change in the systolic minus diastolic (amplitude=AC component); rate of rise or decline of mean flow; dV/dT of changes of diastolic to systolic upslope or systolic to diastolic downslope of individual beats; consistency of the rate of rise or decline, i.e., are there indications of a homeostatic response to counteract the change that is occurring as a result of the drug application?; and/or increase above the physiologic zero value obtained by applying pressure to the tissue beneath the probe so as to eliminate local blood flow.

It is also an object of the present invention to provide a method wherein values may be expressed in a variety of ways, including: absolute readings; percentages versus baseline; percent change on a heart beat to heart beat basis; change relative to that induced by another challenge, e.g., by local warming; and/or ratio of change in amplitude to change in mean or to actual mean.

It is also an object of the present invention to provide algorithms to determine additional indices that may be monitored, including: the development of, or increase of, or loss of oscillations such as those consistent with cholinergic oscillatory control of the microvasculature [see U.S. Patent Application Publication No. 2003/0233048, to Silverman et al., entitled "DETECTION AND CHARACTERIZATION OF CHOLINERGIC OSCILLATORY CONTROL IN PERIPHERAL MICROVASCULATURE".]

It is also an object of the present invention to provide a method wherein the drug that is used for transdermal application for other than the said purpose described herein is adapted for said monitoring described herein. Such adaptation may entail: changing concentration; changing the nature of the drug vehicle (e.g., a micro-patch with backing); changing the light transmission properties of the delivery system; changing the absorptive properties of the drug and delivery system; and/or delivering doses in accordance with the present invention that are effective at the local microvasculature without a remote or systemic effect.

It is also an object of the present invention to provide a method and design/structure/system for assessing blood flow at the level of the microvasculature wherein monitoring entails assessment at a baseline state before the application of a challenge, treatment, or other intervention and/or before the challenge, treatment, or other intervention becomes effective. For example, a pharmacological agent is topically applied to one or more sites on the skin or organ surface; nonpainful, noninvasive, and nondisturbing monitoring of the microcirculation is performed under, within, adjacent to, or through the pharmacological agent; and one or more assessments are made before, during and/or after drug-induced changes in the microcirculation. While this focuses on a method, it is applicable as well to a design, structure and/or system. For example, this may apply to a drug delivery system wherein the system enables effective delivery of desired pharmacologic agent(s) to the tissue under study while enabling effective monitoring before, during, and/or after delivery of desired agent and wherein the system is minimally invasive and, except for agent delivery, minimally disruptive to underlying tissue and its microcirculation.

It is also an object of the present invention to provide a method wherein the mechanism of agent application is a transparent/translucent micro-patch.

It is also an object of the present invention to provide a method wherein the mechanism of agent delivery is a removable micro-patch.

It is also an object of the present invention to provide a method wherein the mechanism of agent delivery is a topically applied gel, ointment, liquid, or cream in accordance with specially adaptive inventive monitoring.

It is also an object of the present invention to provide a method wherein the gel, ointment, liquid, or cream is covered by a covering that enables continuous monitoring while the agent is in place.

It is also an object of the present invention to provide a method wherein the covering that enables continued monitoring is a transparent/translucent drape, thereby constituting a translucent micro-patch that enables continued monitoring with a light transmitting device.

It is also an object of the present invention to provide a method wherein the mechanism of monitoring in the context of a micro-patch entails assessments of red blood cell movement.

It is also an object of the present invention to provide a method wherein the mechanism of monitoring is a laser Doppler flowmeter, a laser Doppler scanner, a laser speckle imager, a plethysmographic measure of volume or flow, or a thermistor.

It is also an object of the present invention to provide a method where the mechanism of monitoring assesses vascular caliber and/or views local capillaries.

It is also an object of the present invention to provide a method wherein the pharmacologic agent is an approved drug with known effects on the cardiovascular system, wherein the pharmacologic agent is one that is not known to have direct effects on the cardiovascular system, or wherein the pharmacological agent is one that has uncertain effects on the cardiovascular system which may prove to be beneficial or harmful.

It is also an object of the present invention to provide a method wherein the agent is designed to induce vasodilation of the blood vessels.

It is also an object of the present invention to provide a method wherein the agent is known to, believed to, or speculated to act as an agonist, antagonist, or other effector at any of the steps in the process of vasodilation, including: neuronal, hormonal or pharmacologic activation or inhibition of endothelial receptors; inhibition of vascular smooth muscle; an/or other mechanism of dilating the vessel(s) in accordance the embodiments of the inventive micro-patch and micro-patch/monitoring systems.

It is also an object of the present invention to provide a method wherein the given drug is believed to cause narrowing of the blood vessels (vasoconstriction), including mechanisms in opposition to those for vasodilation.

It is also an object of the present invention to provide a method wherein the agent is designed to induce endothelium-dependent vasodilation of blood vessels.

It is also an object of the present invention to provide a method wherein the agent that is designed to induce potentially endothelium-dependent vasodilation of blood vessels is an agent with effects such as nicotine.

It is also an object of the present invention to provide a method wherein the agent that is designed to induce endothelium-dependent vasodilation of a blood vessel alters the amount of locally available nitric oxide.

It is also an object of the present invention to provide a method wherein the agent that is designed to induce endothelium-dependent vasodilatation of blood vessels is known to be or believed to be an agonist at muscarinic receptors.

It is also an object of the present invention to provide a method wherein the agent that is designed to induce endothelium-dependent vasodilation of a blood vessel is acetylcholine.

It is also an object of the present invention to provide a method wherein the agent that is being applied to induce endothelium-independent vasodilation is nitroglycerin.

It is also an object of the present invention to provide a method wherein the agent that is being applied to induce endothelium-independent vasodilation is nitroprusside.

It is also an object of the present invention to provide a method wherein the agent acts directly on vascular smooth muscle.

It is also an object of the present invention to provide a method wherein the agent acts indirectly on vascular smooth muscle.

It is also an object of the present invention to provide a method wherein the agent affects blood cell rheology and/or blood viscosity.

It is also an object of the present invention to provide a method wherein the mechanism of analysis includes spectral-domain analysis of alterations in the physiologic waveforms.

It is also an object of the present invention to provide a method wherein the mechanism of spectral-domain analysis includes standard Fourier analysis to assess oscillatory effects.

It is also an object of the present invention to provide a method wherein the mechanism of spectral-domain analysis includes joint time frequency analysis.

It is also an object of the present invention to provide a method wherein the mechanism of analysis includes wavelet transformation, or alternative means of spectral frequency analysis of brief data windows.

It is also an object of the present invention to provide a method wherein the mechanism of analysis includes entropy assessments.

It is also an object of the present invention to provide a method wherein the mechanism of analysis includes assessment of standard time-domain indices such as mean, median, and standard deviation.

It is also an object of the present invention to provide a method wherein the mechanism of analysis includes comparison to changes at a remote reference site.

It is also an object of the present invention to provide a method wherein the mechanism of analysis includes comparison to changes at a remote placebo site.

It is also an object of the present invention to provide a method wherein analysis includes correlation among different sites.

It is also an object of the present invention to provide a method wherein the test is designed to avoid remote effects.

It is also an object of the present invention to provide a method wherein the test is designed to avoid systemic effects.

It is also an object of the present invention to provide a method wherein the subject is also monitored so as to monitor whether local application has an effect on systemic indices such as heart rate and heart rate variability.

It is also an object of the present invention to provide a method wherein the subject is also monitored with respect to blood pressure and blood pressure variability.

It is also an object of the present invention to provide a method wherein the subject is also monitored with respect to blood flow at other sites and blood flow variability.

It is also an object of the present invention to provide a method wherein the test is designed to avoid adverse side effects.

It is also an object of the present invention to provide a method wherein more than one pharmacologic agent is applied to a given site.

It is also an object of the present invention to provide a method wherein the multiple pharmacologic agents are designed to have synergistic and/or antagonistic properties.

It is also an object of the present invention to provide a method wherein the one or more topically applied agents may be given in the context of a systemic challenge.

It is also an object of the present invention to provide a method wherein the systemic challenge is designed to alter the responses of the autonomic nervous system.

It is also an object of the present invention to provide a method wherein the systemic challenge is mental stress.

It is also an object of the present invention to provide a method wherein the systemic challenge is cold pressor testing.

It is also an object of the present invention to provide a method wherein the systemic challenge is hyperventilation.

It is also an object of the present invention to provide a method wherein the systemic challenge is tilting.

It is also an object of the present invention to provide a method wherein the systemic variable is systemic administration of another pharmacologic agent.

It is also an object of the present invention to provide a method wherein the topical and/or systemic agent is phenylephrine.

It is also an object of the present invention to provide a method wherein the topical and/or systemic agent is nicotine.

It is also an object of the present invention to provide a method wherein the topical and/or systemic agent is a phosphodiesterase inhibitor such as sildenafil.

It is also an object of the present invention to provide a method wherein the topical and/or systemic agent is nitroglycerin.

It is also an object of the present invention to provide a method wherein the systemically administered agent is designed to alter the integrity of the endothelium.

It is also an object of the present invention to provide a method wherein the topical and/or systemic agent is an anti-inflammatory medication such as a statin.

It is also an object of the present invention to provide a method wherein the topical and/or systemic agent is an ACE (Angiotensin Converting Enzyme) inhibitor.

It is also an object of the present invention to provide a method wherein the topical and/or systemic agent is an anesthetic agent.

It is also an object of the present invention to provide a method wherein the data are analyzed to assess the status of the microcirculation on one occasion.

It is also an object of the present invention to provide a method wherein the assessments are performed on serial occasions.

It is also an object of the present invention to provide a method wherein the serial assessments are performed to assess the progression or regression of abnormal flow.

It is also an object of the present invention to provide a method wherein the responses of an individual session are assessed individually with paired t-testing or analysis of variance or where they are assessed serially with correlation coefficients and/or regression analysis.

It is also an object of the present invention to provide a method wherein the serial assessments are performed to assess the potential value of a given drug or other form of therapy as a mechanism to improve the microcirculation and/or microvasculature.

It is also an object of the present invention to provide a method wherein the pharmacologic agent is being tested to determine if it may be of value for improving microcirculatory flow.

It is also an object of the present invention to provide a method wherein the agent that is being tested to determine if it will prove microcirculatory flow is being evaluated for potential use as a topically applied therapeutic agent.

It is also an object of the present invention to provide a method wherein the utilization from the aforementioned testing is to design topically effective creams, gels, or ointments to improve perfusion.

It is also an object of the present invention to provide a method wherein the pharmacologic agent is designed to improve perfusion affects one or more of the steps involved with vasodilation.

It is also an object of the present invention to provide a method wherein a pharmacologic agent is designed to increase vasoconstriction.

It is also an object of the present invention to provide a method wherein the agents may be administered to affect (increase or decrease) the release and/or action of nitric oxide.

It is also an object of the present invention to provide a method wherein the agents may be administered to alter the functional integrity of vascular smooth muscle.

It is also an object of the present invention to provide a method wherein the pharmacologic agent designed to improve perfusion is an agent which affects nicotinic receptors such as nicotine.

It is also an object of the present invention to provide a method wherein the pharmacologic agent designed to improve perfusion is an endothelium-dependent vasodilator that affects muscarinic receptors, such as acetylcholine.

It is also an object of the present invention to provide a method wherein the pharmacologic agent designed to improve perfusion is an endothelium-independent vasodilator such as nitroglycerin.

It is also an object of the present invention to provide a method wherein the micro-patches are designed to optimize residence time of the drug at the local site.

It is also an object of the present invention to provide a method wherein the micro-patches are designed to deliver agents which are metabolized rapidly after leaving the local microvasculature.

It is also an object of the present invention to provide a method wherein the micro-patches are designed to deliver agents which are metabolized rapidly after leaving the local microvasculature and that agent is acetylcholine.

It is also an object of the present invention to provide a method wherein the battery of pharmacologic agents are employed to identify the interaction among agents as well as the site of action of a given agent and/or the site of a given abnormality.

It is also an object of the present invention to provide a method wherein the agents may be administered to assess nicotinic receptors.

It is also an object of the present invention to provide a method wherein the agents may be administered to assess muscarinic receptors.

It is also an object of the present invention to provide a method wherein the agents may be administered to assess adrenergic receptors.

It is also an object of the present invention to provide a method wherein the agents may be administered to affect (increase or decrease) the release and/or action of nitric oxide.

It is also an object of the present invention to provide a method wherein the agents may be administered to the functional integrity of vascular smooth muscle.

It is also an object of the present invention to provide a method wherein the aforementioned is applied to assess patients with, or suspected of having, diabetes.

It is also an object of the present invention to provide a method wherein the diabetes has led to autonomic neuropathy.

It is also an object of the present invention to provide a method wherein the diabetes has led to other end organ changes.

It is also an object of the present invention to provide a method wherein the diabetes has not yet led to clinical evidence of end organ changes.

It is also an object of the present invention to provide a method wherein the patient has hypertension.

It is also an object of the present invention to provide a method wherein the patient may be prehypertensive.

It is also an object of the present invention to provide a method wherein the patient is an offspring of hypertensive parents.

It is also an object of the present invention to provide a method wherein the subject likely has a genetic predisposition to hypertension.

It is also an object of the present invention to provide a method wherein the patient has known atherosclerosis.

It is also an object of the present invention to provide a method wherein the patient is suspected of having possible atherosclerosis.

It is also an object of the present invention to provide a method wherein the patient has a pain state which may be caused by altered microcirculation.

It is also an object of the present invention to provide a method wherein the patient has a pain state which may be altering the microcirculation.

It is also an object of the present invention to provide a method wherein the patient has a dermatologic condition which may affect cutaneous blood flow or be affected by altered flow.

It is also an object of the present invention to provide a method wherein the patient has headaches which may have a vascular component.

It is also an object of the present invention to provide a method wherein the patient may have eclampsia of pregnancy or be prone to this disorder.

It is also an object of the present invention to provide a method wherein the magnitude of a response is measured.

It is also an object of the present invention to provide a method wherein the time course of a response is measured.

It is also an object of the present invention to provide a method wherein the concentration or dose of drug that is required to induce a response is quantified.

It is also an object of the present invention to provide a method wherein testing is accompanied by a method/design to ensure that the topical agent has been absorbed.

It is also an object of the present invention to provide a method wherein the method/design to determine drug absorption is a quantitative assay of remaining drug.

It is also an object of the present invention to provide a method wherein the method/design to determine drug absorption is evidence of systemic uptake of the drug.

It is also an object of the present invention to provide a method wherein the method/design to determine drug absorption is a tracer (e.g., radioactive or fluorescent) with the drug to determine uptake.

It is also an object of the present invention to provide a method wherein a patient would be tested to determine the likely responsiveness to topical application of a given drug wherein the tissue to be treated is ischemic or potentially ischemic.

It is also an object of the present invention to provide a method wherein a patient would be tested to determine the likely responsiveness to topical application of a given drug wherein the ischemic or potentially ischemic tissue is affected by peripheral arterial disease.

It is also an object of the present invention to provide a method wherein a patient would be tested to determine the likely responsiveness to topical application of a given drug wherein the potentially ischemic tissue is a skin flap.

It is also an object of the present invention to provide a method wherein the patient is tested to determine likely responsiveness of systemic administration of a given drug.

It is also an object of the present invention to provide a method wherein such information is used to guide therapy in patients with potential tissue injury or end organ damage.

It is also an object of the present invention to provide a method wherein such information is used to guide therapy in patients with a local vascular abnormality.

It is also an object of the present invention to provide a method wherein such information is used to guide therapy in patients with a systemic cardiovascular abnormality.

It is also an object of the present invention to provide a method wherein the patient is instructed to breathe at a fixed rate so that the impact of respiration on oscillatory activity can be identified and possibly isolated.

It is also an object of the present invention to provide a method wherein a portion of baseline is compared to a portion of the period during and/or the time of drug delivery.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 10A shows the opening.

FIG. 10B shows how monitoring can be accomplished via the opening. FIGS. 10C and 10D show how drug delivery may be accomplished not only by simply applying drug via the opening but also viewed microtubules which enable delivery to the opening as well as to other areas beneath the micro-patch.

DESCRIPTION OF THE PREFERRED EMBODIMENTS

Figure 1:
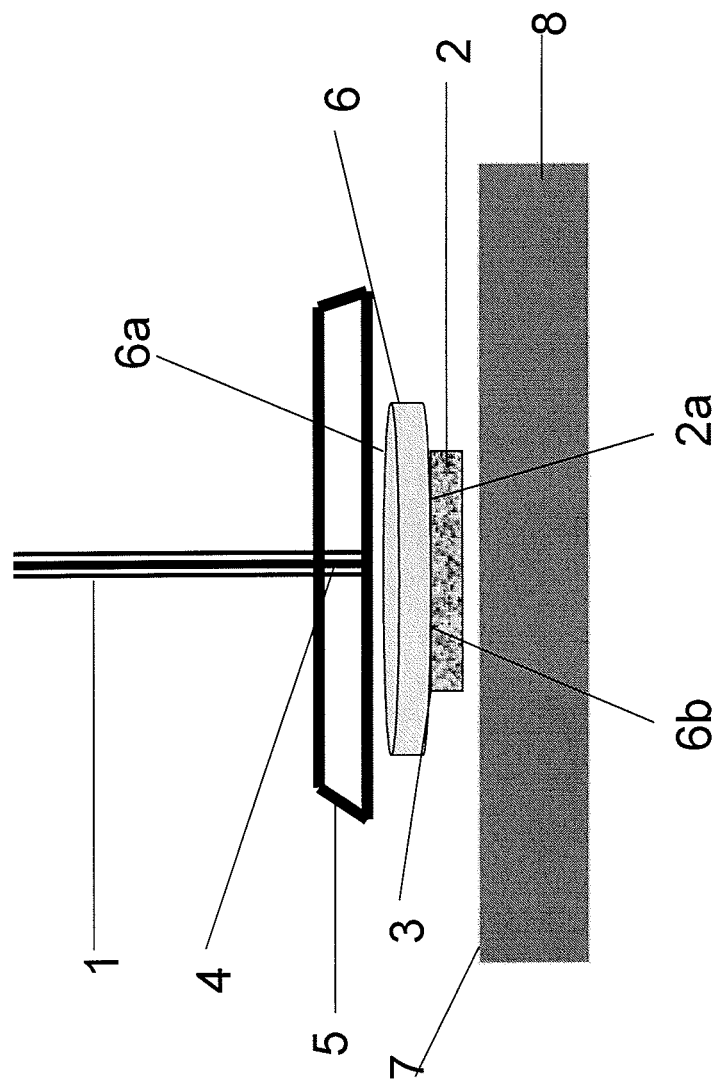
FIG. 1 is a schematic illustrating a preferred embodiment in accordance with the present invention which shows a laser Doppler flowmetry probe (with its end in a probe holder) atop a double-sided adhesive ring and a micro-patch for adherence to a study site.

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

The present invention provides a repeatable, noninvasive, nonintrusive and readily applicable test to interrogate and study the microcirculation of a subject in multiple regions and thereby characterize their function in health and disease, monitor changes in the microcirculation over time, and identify responses in the microcirculation to potentially harmful or beneficial interventions. The present invention introduces apparatuses and methods for: a) focused assessment of the microvasculature that entails noninvasive trans-surface (e.g., transdermal) delivery of a study agent (e.g., a drug with potential microcirculatory effects) and b) a mechanism for noninvasive and repeatable localized monitoring of the microvasculature at the site(s) of agent delivery as well as at untreated sites. The present invention also provides a mechanism for transdermal drug delivery and local assessment of the microcirculation.

This is achieved by providing a method for interrogating the microcirculation of a subject for use in characterizing function in health and disease, monitor changes in microcirculation over time, and identify responses in microcirculation to potentially harmful or beneficial interventions. The method includes delivering a study agent to a study surface for trans-surface delivery to the 2 microvasculature of the subject in a non-iontophoretic manner and monitoring the microvasculature of the subject in the area of the study surface. A system is also provided which includes a micro-patch for delivery of a study agent to a study surface for trans-surface delivery to the microvasculature of the subject in a non-iontophoretic manner and a monitoring probe for monitoring the microvasculature of the subject in the area of the study surface.

The present invention generally relates to a mechanism for local delivery of vasoactive medications and combinations thereof which enable effective monitoring of local vasoreactivity without unwanted systemic effects, a customized modification of monitoring techniques and devices to optimize such testing and a mechanism for interpreting the findings. As used throughout the present disclosure, the terms "drug", "agent" and "study agent" are used to generally refer to a wide variety of vasoactive or potentially vasoactive substances that may be employed in accordance with the present invention.

Such interrogation of the local microvasculature has multiple significant clinical implications in that microvascular dysfunction has been observed in patients with a wide variety of disorders including: diabetes (leading to diabetic end-organ disease such as retinopathy, nephropathy, neuropathy, cardiac disease and stroke), atherosclerosis, coronary artery disease, peripheral vascular disease, hypercholesterolemia, hypertension, cigarette smoking, and varied pain states. There is evidence to suggest that dysfunction of microvascular endothelium in an accessible area, such as the skin, correlates with vascular injury throughout the body, including the heart. Anderson T J: Assessment of endothelial function: research tool or clinical reality? Cardiology Review: Endothelial Function Forum CME, July 1999; Anderson T J, Meredith I T, Yeung A C, et al. The effect of cholesterol-lowering and antioxidant therapy on endothelium-dependent coronary vasomotion. N Engl J Med 1995; 332:488; Anderson T J, Overhiser R W, Haber H, Charbonneau F. A comparative study of four anti-hypertensive agents on endothelial function in patients with coronary disease. J Am Coll Cardiol 1998; 31:327A, Abstract #1147-54; and Anderson T J: Assessment of endothelial function: research tool or clinical reality? Cardiology Review: Endothelial Function Forum CME, July 1999. The availability of a repeatable, noninvasive, nonintrusive and readily applicable test as disclosed in accordance with the present invention facilitates identification of a disorder, documentation of its course, and the effect of therapy. As discussed above in the Background of the Invention section, prior to the present invention, a desired mechanism of interrogating the microvasculature in this manner has not been available.

As will be discussed below in greater detail, the present invention employs "micro-patches" (or mini-patches) for selective, local transdermal delivery of vasoactive (and placebo) medications without the need for local injection or application of a driving electric (iontophoretic) current. These contain predetermined and customized consistencies and concentrations of a drug (or biologically active agent) in ointment, gel, cream or liquid for application in customized sizes and shapes. While examples of sizes are included herein, in most embodiments, the main limit on the micro-patch is that it be a size, dose, concentration and vehicle that enables local testing without a systemic effect. Alternatively, the size should not be smaller than the sensing area of the monitoring probe. Micro-patches that are larger than desired can be used with a means for blocking drug access to the study site, such as by use of an impenetrable disk (for example, a double-sided adhesive ring 6 as discussed herein) beneath the micro-patch that only allows exposure of 59.4-mm$^2$ of the micro-patch.

To enable effective transmission of light signals for light transmission monitoring techniques, and as will be discussed below in greater detail, the basic inventive "micro-patch" may contain: a) a transparent, translucent or clear backing to enable monitoring through the micro-patch; or b) microfibrils coursing to the monitoring site atop, within and/or below the micro-patch.

Figure 3:
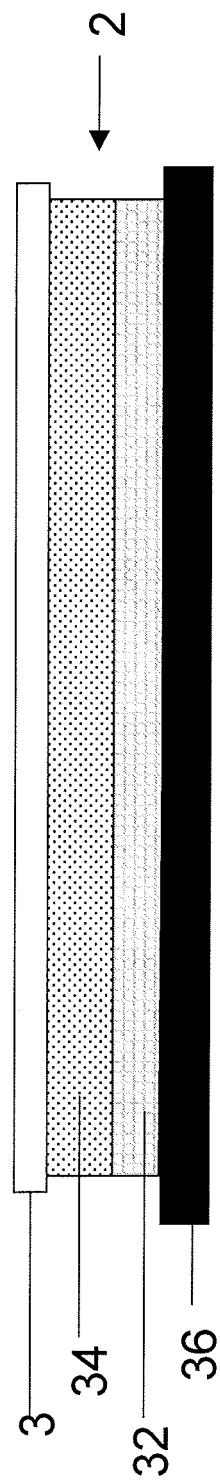
FIG. 3 is a schematic showing a micro-patch in accordance with the present invention with layers showing an inactive layer/matrix that can be customized to delay delivery of drug (or biological agent) and enable baseline readings with the micro-patch in place.
Figure 4:
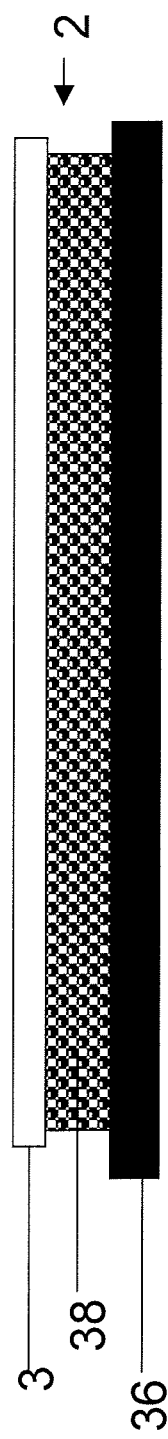
FIG. 4 is a schematic showing a micro-patch in accordance with the present invention with the drug encapsulated to delay its delivery and/or its release after delivery.

Delivery of agent via micro-patch may occur in a variety of ways: a) drug that is active prior to application of monitoring (not preferred because of need for baseline values at the site of drug administration); b) by delayed release from the micro-patch with clear backing as shown with reference to the embodiments in FIGS. 3, 4, 5A and 5B, and as discussed below in greater detail; c) delayed activation of an encapsulated drug such as that shown in FIG. 4 (as by body temperature, chemicals, external ultrasound) after it is delivered; and d) delivery via microfibers that course above, within or below the mini-patch (regardless of backing) as shown with reference to the embodiments in FIGS. 6 and 7 and as discussed below in greater detail.

It is contemplated the micro-patch may have an opening or gap to permit application of another agent and/or to facilitate monitoring while the micro-patch is in place. Although preferred embodiments as described herein set forth the application of the micro-patch to the skin of a subject, it is contemplated application of the micro-patches is not limited to the skin, and may include mucosal surfaces or the surface of another body tissue.

It is further contemplated, alternative embodiments may more aptly be referred to as "micro-applicants" that are composed of an aliquot of agent/vehicle without backing. Those applied solely to the skin may be referred to as "micro-derm applicants." For purposes of simplicity, all are referred to herein as "micro-patches."

Figure 16:
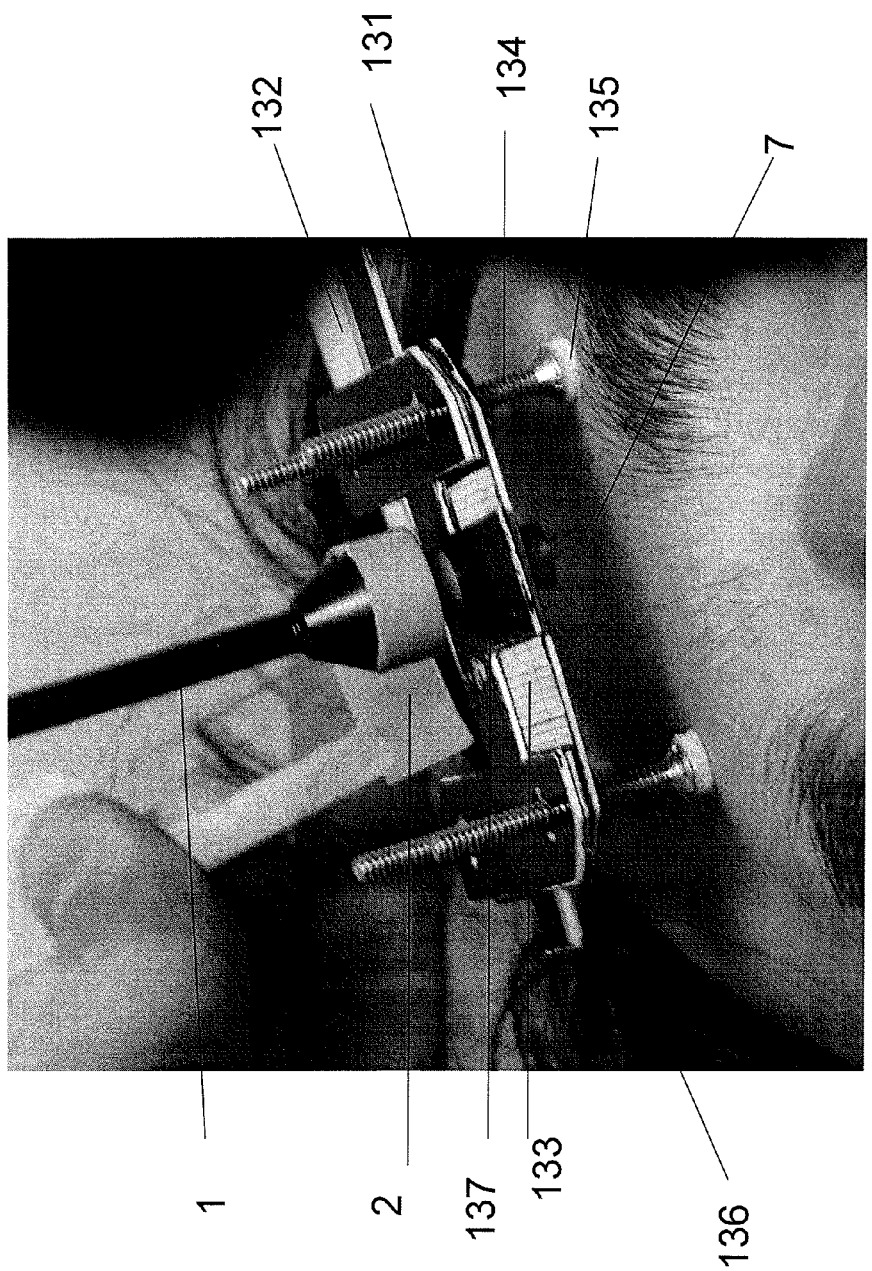
FIG. 16 is a perspective view showing a probe support assembly for mounting a probe (in this case a multichannel probe) above the skin. The support assembly is designed to enable consistent movements in fixed increments (e.g., 1 mm) so as to obtain new measurements without disturbing the alignment of the probe with the skin or an underlying micro-patch. In practice, and as will be discussed below in greater detail, the probe remains undisturbed while a micro-patch is being placed in alignment under the probe.

In order to avoid the need to remove monitoring probes for drug application after baseline unless the micro-patch enables delayed release, the application of a micro-patch after baseline is best obtained in embodiments where the monitoring is elevated above the skin as shown for a probe in FIG. 16 and for a noncontact device as a scanner in FIGS. 22-25.

The inventive micro-patch is designed so as to constitute one of several different embodiments, with the following inventive features:
sufficient agent and agent delivery to affect the underlying microvasculature, with limited agent delivery so as to prevent unwanted changes at remote sites or undesirable systemic uptake;
a configuration that enables monitoring of the local microvasculature; e.g., a transparent backing that enables transmission of light signal for laser Doppler flowmetry, laser speckle imaging, and/or photoplethysmography; and
a configuration that ensures effective delivery throughout the potential areas of the monitoring site.

Figure 12:
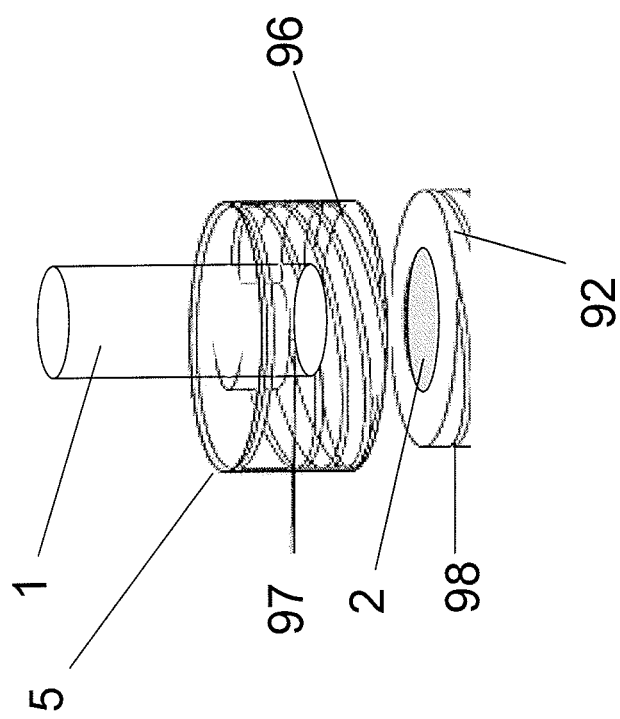
FIG. 12 is a perspective view of a schematic showing a two-component mechanism for engaging and advancing a laser Doppler flowmetry probe. The probe is in a probe holder with threads (or grooves) for threaded engagement with threads on the circumference of a disc encasing the micro-patch. Advancements secure the laser Doppler flowmetry probe and pushes the micro-patch against the study site.
Figure 13:
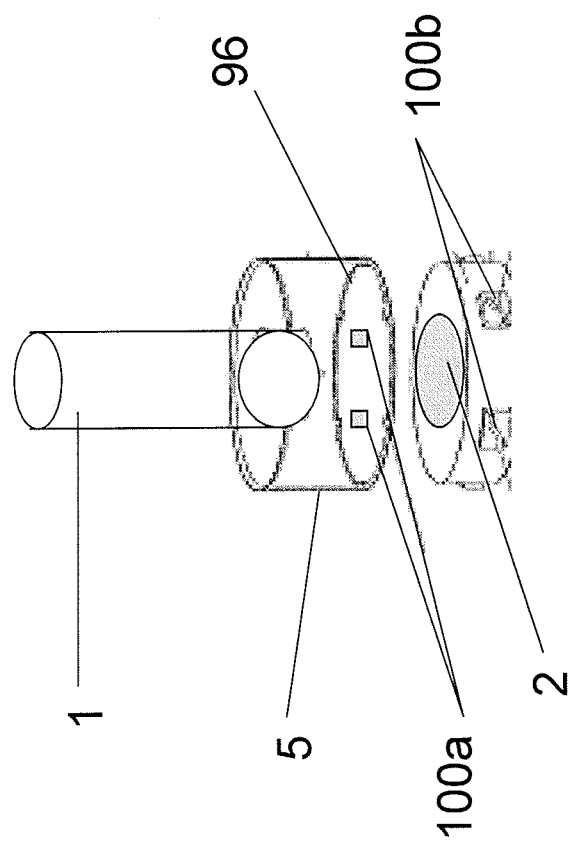
FIG. 13 is a perspective view of a schematic showing an alternative mechanism for advancing and engaging a laser Doppler flowmetry probe into a probe holder and pushing the micro-patch against the study site. Here, the probe is encased in a probe holder with tabs on the inside of its outer rim. These engage interspaced threads on the circumference of the disc encasing the micro-patch.
Figure 14:
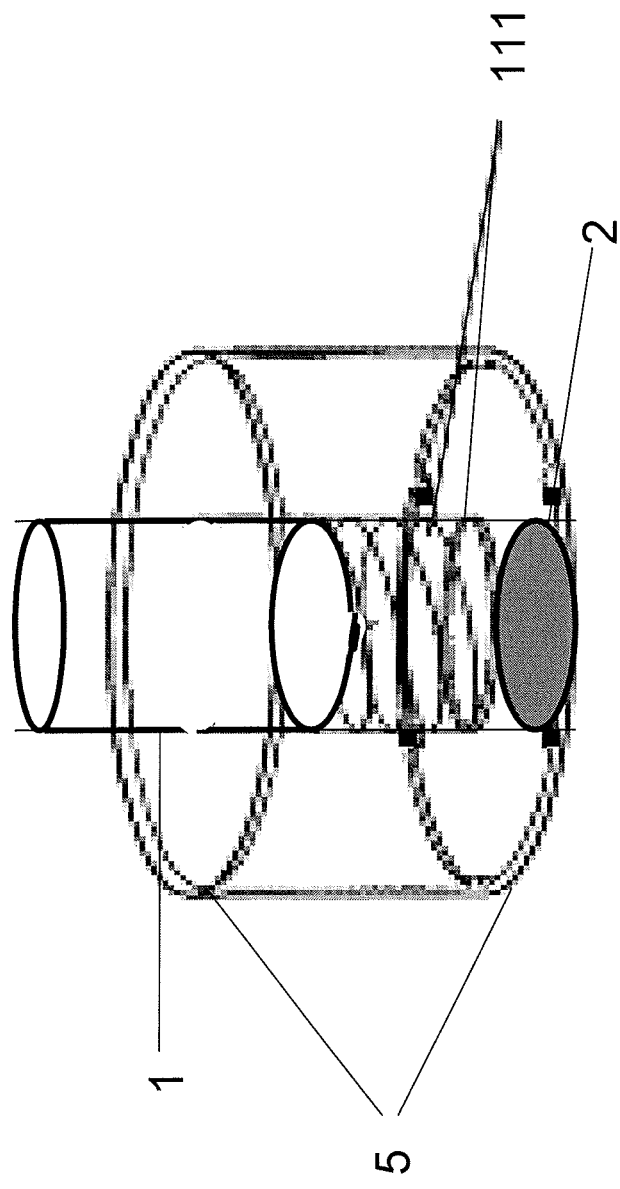
FIG. 14 is a schematic showing a laser Doppler flowmetry probe holder which is separated from the study surface by a spring. After baseline readings are obtained with the micro-patch lying gently on the study surface beneath the spring, the probe and its probe holder are advanced to transiently compress the spring and increase adherence of the micro-patch. Tabs on the probe holder are shaped and dimensioned for threaded engagement with threads on the probe holder (as shown in FIG. 11). Multiple alternatives for comparable engagement and disengagement previously have been described by the inventor (with respect to engaging needles and diaphragms) in U.S. Pat. No. 6,391,014, to Silverman, entitled "STRONG DIAPHRAGM/SAFE NEDDLE/CONVERTING DEVICE COMBINATIONS AND THEIR INDIVIDUAL COMPONENTS", issued May 21, 2002, which is incorporated herein by reference.

In accordance with preferred embodiments, the micro-patch may have one of several potential mechanisms to regulate agent delivery so as to:
enable real-time dose-response assessments; and
allow for baseline readings prior to inducing a drug response by:
delaying release of drug from micro-patch already in place—as by encapsulating agent, including an inactive preliminary layer, including a dissolvable membrane;
delaying adherence of micro-patch to study site until probe is advanced, as shown in FIGS. 12-14; and/or
delaying delivery of drug to the study site by applying the micro-patch after baseline readings are obtained (as facilitated by a probe that is elevated above the study site as shown in FIG. 16) and/or delaying delivery via embedded tubules or gaps in the micro-patch (as shown in FIGS. 7 and 10A-D). The aim is to enable attainment of baseline data without the need to displace the monitoring equipment to subsequently initiate agent delivery. Additionally, a strip, such as that shown in FIGS. 6 and 7, could be partially peeled back (while remaining anchored in place) so as to allow micro-patch application (if the agent were not already a component of the strip).

An inventive micro-patch may deliver:
a) an agent that previously has not been available for transdermal administration;
b) an agent that, although previously available for transdermal administration, has not been available as a patch for drug delivery; and/or
c) an agent which is available as a patch for transdermal delivery but which has not heretofore been adapted or utilized for the monitoring of the local microvasculature (or testing its efficacy at the level of the microvasculature). As of this time, except for those disclosed by the inventor (and colleagues under his direction), no patch has been designed for use in the manner described herein in accordance with a preferred embodiment of the present invention.

With respect to "a" above, and in accordance with a preferred embodiment of the present invention, the apparatuses and methods are introduced and described for transdermal ("trans" tissue surface) administration of acetylcholine and phenylephrine; two drugs not previously available for passive transdermal administration (i.e., that previously required injection into a patient's artery or iontophoretic delivery with an electric current as discussed above in the Description of the Related Art section above). The advantages of this approach are described later in the present disclosure. It is contemplated the present introduction of transdermal delivery of drug for localized testing of the microvasculature with a given dose of a given agent could readily be adapted to other doses as well as to other agents based upon the teachings provided herein. Specifically, this approach may be applied to any or all of the steps involved in vasoconstriction or vasodilation of the microvasculature, including:
   activation or inactivation of receptors;
   activation or inhibition of contraction or relaxation of vascular smooth muscle;
   production, secretion, removal, or metabolic degradation of vasoactive substances such as nitric oxide, prostacyclin, endothelin, platelet-activating factor; thrombin, bradykinin, ADP and ATP; and/or
   alteration by inflammatory mediators.

With respect to drugs that already are used for transdermal administration ("b" and "c" above), the present disclosure describes methods, apparatuses, systems, and structures for modifying such agents for the purpose of testing the local without remote or systemic changes and undesirable systemic side effects from local drug application.
   The micro-patches may be applied for:
   testing at small area(s) of seemingly healthy tissue;
   testing at multiple areas of healthy tissue with comparable innervation (e.g., relative sympathetic and/or parasympathetic neurovascular control) and perfusion so as to compare responses to the same micro-patches, responses to different micro-patches, and/or to responses to a micro-patch at one site and a different challenge;
   testing at multiple areas of healthy tissue with different innervation and/or perfusion to document the vasoreactive properties of the given regions;
   testing of multiple agents and/or challenges at a given site; and/or
   testing at multiple sites with different, unknown or uncertain vessel and tissue integrity (e.g., one site might be injured and/or have compromised healing). Comparisons may entail responses to the same micro-patch, different micro-patches, and/or other challenges.
   More specific examples include:
   Evaluate local vasoactivity and vasoreactivity in diseases such as diabetes, hypertension, and other disorders with a possible vascular component and to characterize the nature of dysfunction based on responses to different agents (e.g., neural, receptor, endothelium-dependent, endothelium-independent) as well as the effects of therapeutic interventions on the responses at said site. An inability to dilate effectively may signal significant dysfunction with potential tissue injury.
   Enable assessment of a topically applied drug in the context of a systemically administered drug or a systemic challenge. This constitutes a unique "dual platform" for assessing the interaction of multiple drugs such as nitroglycerin and sildenafil (Viagra) wherein one or more drugs could be administered via micro-patch and thereby avoid dangerous systemic levels of two drugs.
   Document the potential therapeutic effectiveness of topical application of a drug designed to alter perfusion and potentially improve healing by monitoring effects on local perfusion.
   Test microcirculatory vasoactive effects not only of precedented medications (i.e., those with established mechanisms of action) but also of unprecedented medicines.
   Determine if a given therapy or intervention has an undesirable effect on the micro circulation:
      whether said agent is to be both applied and assessed locally; or
      whether it is to be administered systemically and assessed locally with respect to its effect on the response of the local microvasculature to the contents of a given micro-patch.
   Two prominent, costly examples where testing has not been performed and which may be appropriate for testing in accordance with the present invention are:
      the adverse effects of COX2 inhibitors such as rofecoxib (Vioxx, Merck) may have been identifiable by the present invention before its unexpected adverse effects on the microvasculature (causing increased risk of fatal heart injury) became evident during clinical use and caused prompt withdrawal from the market and multiple high-profile law suits; and
      the adverse effects of torcetrapid (Pfizer) that were not appreciated until relatively late during a 15,000 patient clinical trial (increased cardiovascular morbidity and mortality) may have been identifiable by utilization of the present invention. The drug-induced hypertension may have been due to compromised vasodilatory activity. Use of the present invention also may have identified the vascular abnormality that led to increased signs and symptoms of coronary artery disease. Instead Pfizer was startled by the discovery. According to the Dec. 4, 2006 *Wall Street Journal* ("Demise of a blockbuster drug complicates Pfizer's revamp"), just two days earlier, Pfizer's research chief stated, "We believe this is the most important new development in cardiovascular medicine in years." The sudden and surprising discovery of adverse effects led to a precipitous halt of the study and a double-digit decline in Pfizer stock.
   Predict whether a given tissue will be able to meet demands for increased perfusion as may be required if the patient is scheduled to undergo surgery at that site (and thus need an increase in blood flow to heal the surgical wound).

As discussed below in greater detail, appropriate drug selection enables delineation of the nature of a vessel abnormality. For example, one can compare the effects of nitroglycerin and acetylcholine:
   Nitroglycerin is a nitric oxide donor that causes relaxation of vascular smooth muscle and hence dilation of blood vessels even if the inner endothelial lining of the vessel is damaged; hence it causes endothelium-independent vasodilation.
   Acetylcholine is an agent which activates receptors on intact endothelium that then cause local release of nitric oxide; hence it requires an intact endothelium and thereby causes endothelium-dependent vasodilation.

To the best of the inventor's knowledge, no one has previously disclosed an apparatus or method for noniontophoretic transdermal (trans-surface) delivery of vasoactive agents via translucent micro-patches (or their equivalent) for interrogation of the at the site of drug application. While the present invention is considered to represent the first use and adaptation of transdermal micro-patches for the purposes described herein, patches have previously been used in clinical settings. The differences from the prior art include:

the present invention provides for preparations of agents that previously were not used for such passive transdermal delivery (e.g., for transdermal delivery of acetylcholine);

the present invention provides methods and apparatuses for achieving a local (nonremote, nonsystemic) microvascular effect of transdermal preparation;

the present invention provides mechanisms for monitoring the effect of the application of the micro-patches; and testing and apply varying concentrations of agent, including concentrations much greater than those used for standard care with the given agent. This is possible because the micro-patch limits total dosages and hence systemic and remote drug levels. Any adverse local effects from high doses would readily be detected by real-time monitoring.

Referring to FIG. 1, a system for implementing the present invention entails the application and positioning of a laser Doppler flowmetry probe 1 (or comparable transmitting/receiving monitoring device (or probe) such as a laser Doppler scanner, laser speckle or photoplethysmograph) above a micro-patch 2 with a transparent or translucent backing 3. As shown in FIG. 1, the patient end 4 of the laser Doppler flowmetry probe 1 is enclosed in, and supported by, a probe holder 5. One of the potential alignments in accordance with a preferred embodiment of the present invention, as shown in FIG. 1, entails attachment of a first side 6a of a double-sided adhesive ring 6 (or comparable double stick interface) to the probe holder 5 and the other, or second, side 6b of the double-sided adhesive ring 6 to the top surface 2a of the translucent micro-patch 2 with desired agent.

Figure 2:
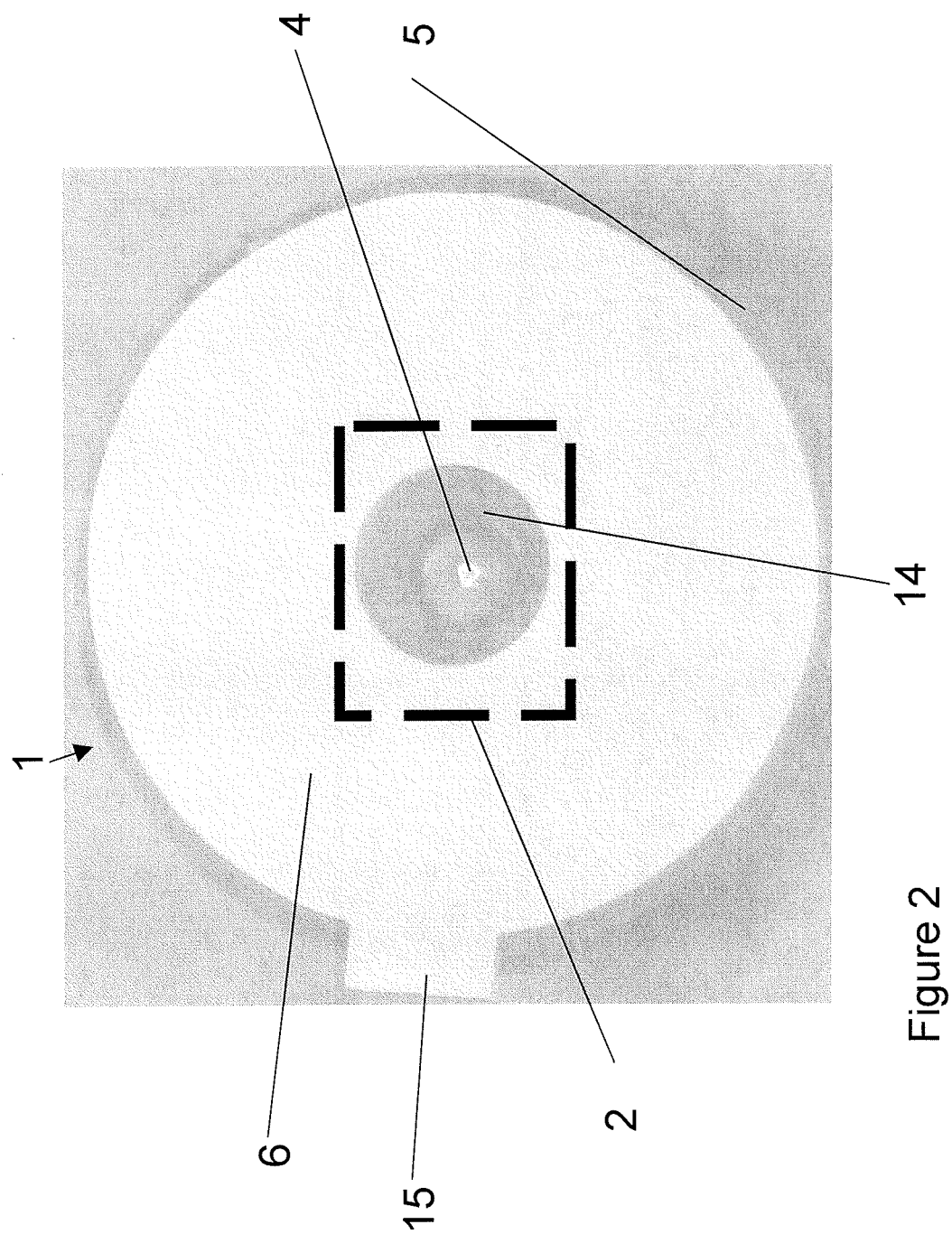
FIG. 2 is a plan view from below the end of an alternate embodiment with a laser Doppler flowmetry probe, micro-patch (shown by broken lines as it is transparent and covered by the double-sided adhesive ring), and double-sided adhesive ring (whose patient surface remains covered). In accordance with a preferred embodiment, the micro-patch (rectangle outlined with broken line) is slightly larger than the desired delivery area; it therefore is placed between the encased laser Doppler flowmetry probe and the double-sided adhesive ring such that the rim around the ring opening controls the area of drug exposure.

In accordance with a preferred embodiment of the present invention, and as shown with reference to FIG. 2, the first side 6a and second side 6b of the double-sided adhesive ring 6 are provided with cover members 15 (only shown attached to the second side 6b in FIG. 2), which are selectively removed from the double-sided adhesive ring 6 when desired for use in accordance with the present invention. The cover members 15 help protect the double-sided adhesive ring 6 from inadvertently sticking to anything prior to attachment to the probe holder 5 and the micro-patch 2. The micro-patch 2 and double-sided adhesive ring 6, which as shown in FIGS. 1 and 2 extends beyond the periphery of the micro-patch 2, both of which may contain adhesive, are ultimately attached to the surface 7 of the tissue 8 under study. The adhesive in the micro-patch 2 can be mixed with the agent(s) to be delivered or in agent-free zones.

FIG. 2 is a view from below which illustrates a slight modification of the embodiment shown with reference to FIG. 1, that is, the order of the micro-patch 2 and double-sided adhesive ring 6 are switched such that the micro-patch 2 is positioned between the probe 1 and the double-sided adhesive ring 6. Light is shown emerging from the distal end (or patient end) 4 of the laser Doppler flowmetry probe 1 in its probe holder 5. In the embodiment shown in this figure, the micro-patch 2 is larger than the actual site of measurement; therefore, its area of delivery is limited by a mechanism such as the double-sided adhesive ring 6, with a central opening 14. More particularly, the micro-patch 2 is positioned between the probe 1/probe holder 5 and the double-sided adhesive ring 6 with the ring 6 creating a barrier between the micro-patch 2 and the study surface 7 where contact between the micro-patch 2 and the study surface 7 is limited to the area permitted by the central opening 14 formed in the ring 6. The adhesive patient surface of the double-sided adhesive ring 6, and micro-patch 2, can be applied to the study site after its cover member 15 is removed.

As various micro-patch embodiments are described herein, similar reference numerals will be used to designate similar components of these various embodiments. In accordance with a preferred embodiment(s), the drug-containing micro-patch 2 is a quantifiable thin layer of a transdermal preparation, preferably in the form of an individual button-sized unit (typically approximately 0.25 cm to approximately 2.5 cm diameter, tailored to the size of the site to be monitored), a peel-away button-sized unit from a larger strip, or a button-sized punchout from a larger patch. The dose of agent applied to the study surface 7 by the micro-patch 2 will be low enough to preclude the potential for significant systemic levels of drug as may be confirmed by measurement of blood levels, systemic effects or changes at a remote site (unless one deliberately selects a dose that enables detection of systemic or remote effects). For each drug/vehicle combination, the minimally effective dose and maximum nonsystemic dose may be determined in dose-response studies as would typically characterize introduction of a new drug or new means of delivery.

Whereas prior art patches and other forms of agent delivery are designed to accelerate initial delivery of drug, preferred embodiments of the present invention seek to delay initial delivery so as to enable attainment of baseline data. In order to permit assessment of baseline and post-drug states without the need to move the monitoring probe, that is, the laser Doppler flowmetry probe in accordance with a preferred embodiment of the present invention, 1, preferred embodiments of the micro-patch 2 may delay delivery of the drug or agent. For example, and as discussed below in greater detail, in accordance with a preferred embodiment of the present invention, the delivery of a nicotine micro-patch 2 is delayed for 10-20 minutes by placing a commonly applied translucent dressing (e.g., a TEGADERM) beneath the micro-patch 2. As shown in FIG. 3, delayed delivery may also be achieved by constructing the micro-patch 2 with an inert layer, such an inactive matrix 32, or a rate-controlling film on the patient side of the active layer 34. Referring to FIG. 4, delayed delivery of the drug or agent is achieved by constructing a micro-patch 2 with the drug encapsulated in a carrier vehicle 38, such as, dissolvable or destructible capsules. In addition, it is contemplated the delayed delivery of drug may be achieved by altering solubility as by interaction with a "linker," or conversion of an inactive to active ingredient. In particular, the micro-patch 2 as shown in FIG. 3 includes layers progressing from a clear (or transparent) backing 3, to agent to be delivered 34, to an inactive layer/matrix 32 that can be customized to delay delivery of the drug, to a protective cover member 36 that is removed just prior to application of the micro-patch to a subject. The micro-patch shown in FIG. 4 includes layers progressing from a clear backing 3, to the drug encapsulated in a carrier vehicle 38 to delay its delivery to a protective cover member 36 that is removed just prior to application of the micro-patch to a subject. With regard to the embodiment described above with reference to FIG. 1, the clear backing 3 is secured to the double-sided adhesive ring 6 for attachment to the probe holder 5 while the inactive layer/matrix 32 or the drug encapsulated in a carrier vehicle 38 is oriented for placement directly upon the study surface 7.

Figure 5A:
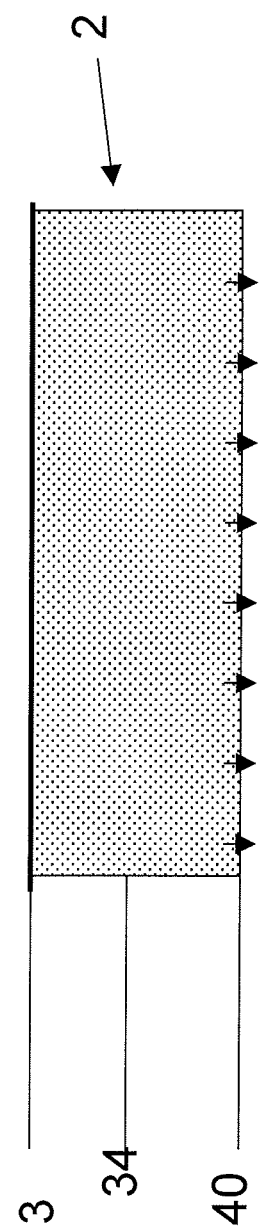
FIG. 5A is a schematic of an alternate embodiment showing a micro-patch with projections directed toward the skin so as to increase drug penetration. The projections may be solid or hollow microtubules.
Figure 5B:
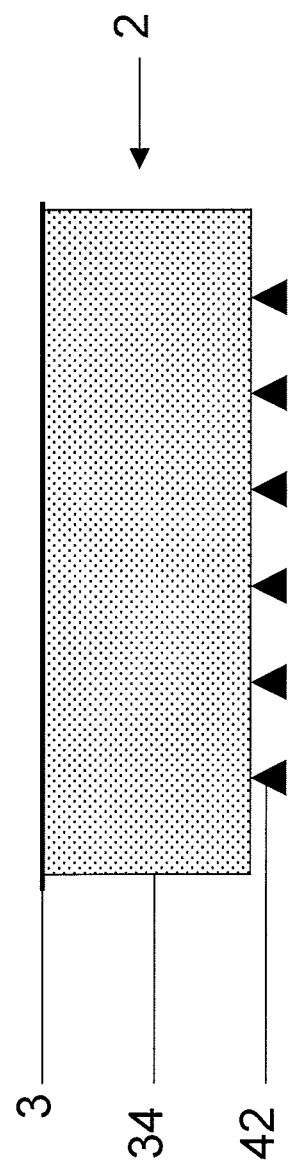
FIG. 5B is a schematic of an alternate embodiment showing an inventive array of projections—directed toward the micro-patch—so as to convert the micro-patch from baseline to drug delivery states. As with the embodiment shown with reference to FIG. 5A, the projections may be solid or hollow.

Additionally, and with reference to FIG. 5A, the micro-patch 2 is provided with drug-coated mini-projections 40. This embodiment utilizes drug-coated mini-projections 40, for example, those provided by of Alza Corporation's Maxroflux® Transdermal Technology, to create superficial pathways through the skin's dead barrier layer allowing transport of macromolecules via micro-patch 2. As with the prior embodiments, the micro-patch 2 includes layers progressing from a transparent backing 3, to the drugs contained in the active layer 34, to the mini-projections 40 permitting delivery of drugs contained in the active layer 34. FIG. 5B illustrates an inventive modification of the miniprojection technology, such that reverse projections 42 extend into the micro-patch 2 to open up channels for agent delivery and/or dissolve capsules or other means that have delayed drug delivery. As with the embodiment disclosed with reference to FIG. 5A, the micro-patch 2 includes layers progressing from a transparent backing 3, to the drugs contained in the active layer 34, to the reverse projections 42 permitting delivery of drugs contained in the active layer 34.

The present invention introduces a 2-step process for the mini-projection technology, wherein the first step involves placing the micro-patches 2 gently on the study site surface and the second step entails initiating (or markedly increasing) delivery upon advancement of the monitoring probe 1. The apparatuses and methods to achieve this are described below with reference to FIGS. 11-14 that are discussed below in greater detail.

Figure 6:
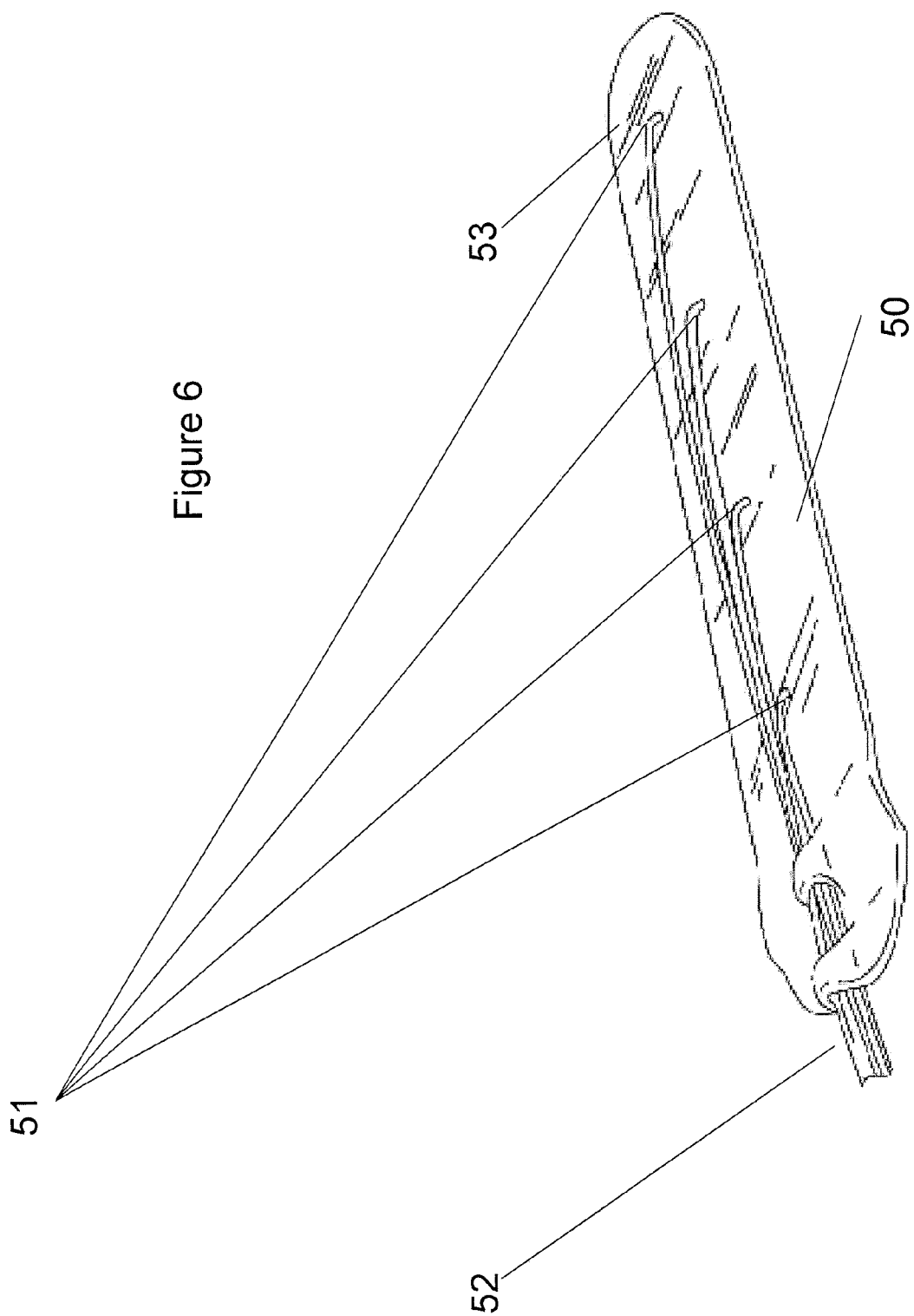
FIG. 6 is a perspective view of an alternate embodiment showing a strip micro-patch with microfibers to enable persistent monitoring and consistent positioning while the micro-patch is in place.
Figure 7:
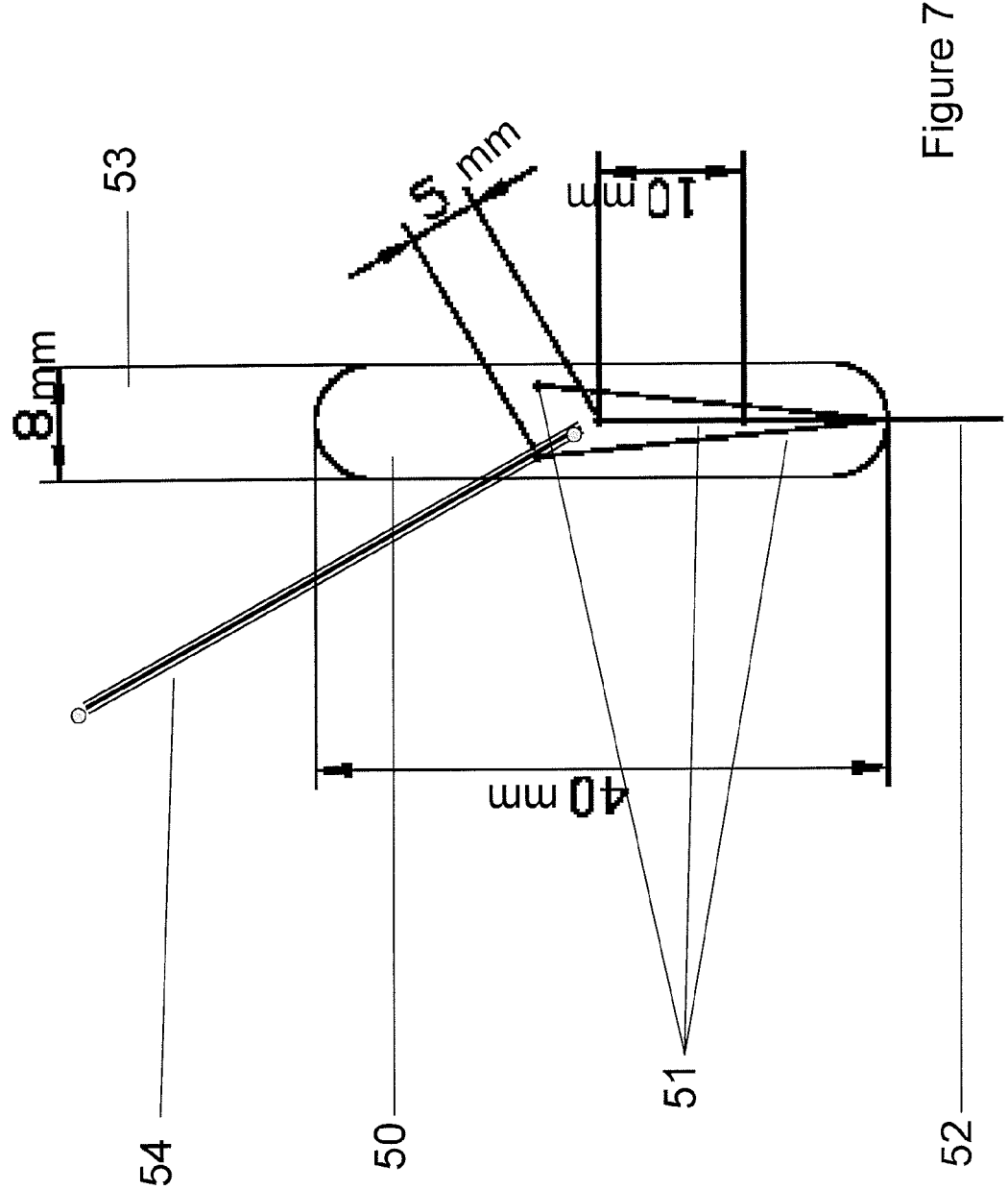
FIG. 7 is a schematic of an alternate embodiment showing a micro-patch with microfibers in an alternative pattern and also demonstrates how a similar channel may be used to deliver agent to one or more microfiber monitoring sites.

An alternative micro-patch 2 configuration is shown with reference to FIGS. 6 and 7. The prior art includes mechanisms to embed microfibers within or below a plastic strip before directing downward for implantation on the brain surface. The present invention adapts that technology to the inventive micro-patch. In accordance with a preferred embodiment of the present invention, a typical plastic strip 50 is customized to include light-transmitting fibers 51 (approximately 0.25-0.45 mm diameter in accordance with a preferred embodiments) in a desired array (for example, four fibers as shown with reference to FIG. 6, three fibers as shown with reference to FIG. 7) for use in monitoring the microcirculation. The microfibers are grouped in a bundle as they leave the strip 50 for connection to separate laser Doppler channels. In accordance with preferred embodiments, the strips 50 themselves are constructed in the form of the micro-patches 2, as illustrated in FIGS. 1, 3, 4, 5A and 5B (with the addition of light transmitting fibers as discussed above) and delivery study agent to a study site. The micro-patches need not be translucent. The embedded microfiber construction offers another potential advantage: it can be anchored (e.g., with adhesive) at one end 53 so that, after baseline readings are obtained, a portion of the strip 50 can be lifted to enable application of a micro-patch 2 at one or more study sites and then replaced without causing a shift in microfiber orientation (and thus constitute one of several ways described in the present disclosure to minimize the impact of spatial heterogeneity). FIG. 7 introduces another potential feature of several embodiments: an embedded microtubule 54 for infusion of agents.

Figure 8:
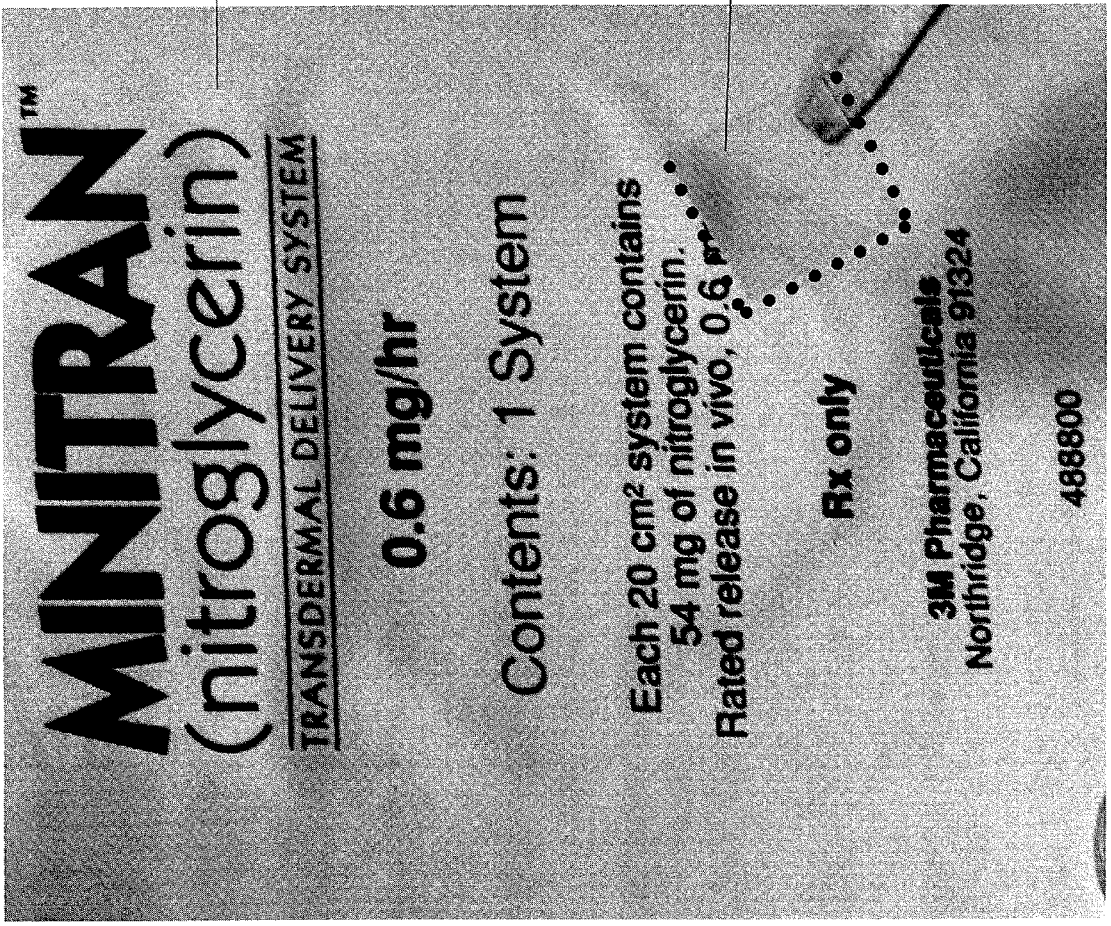
FIG. 8 is a front plan view photograph showing the size of a nitroglycerin micro-patch in accordance with the present invention compared to a package containing a full-size patch. The rectangle shown here enables monitoring over an area greater than that covered by a standard stationary probe. For a stationary probe, a button-shaped micro-patch typically is sufficient.
Figure 9:
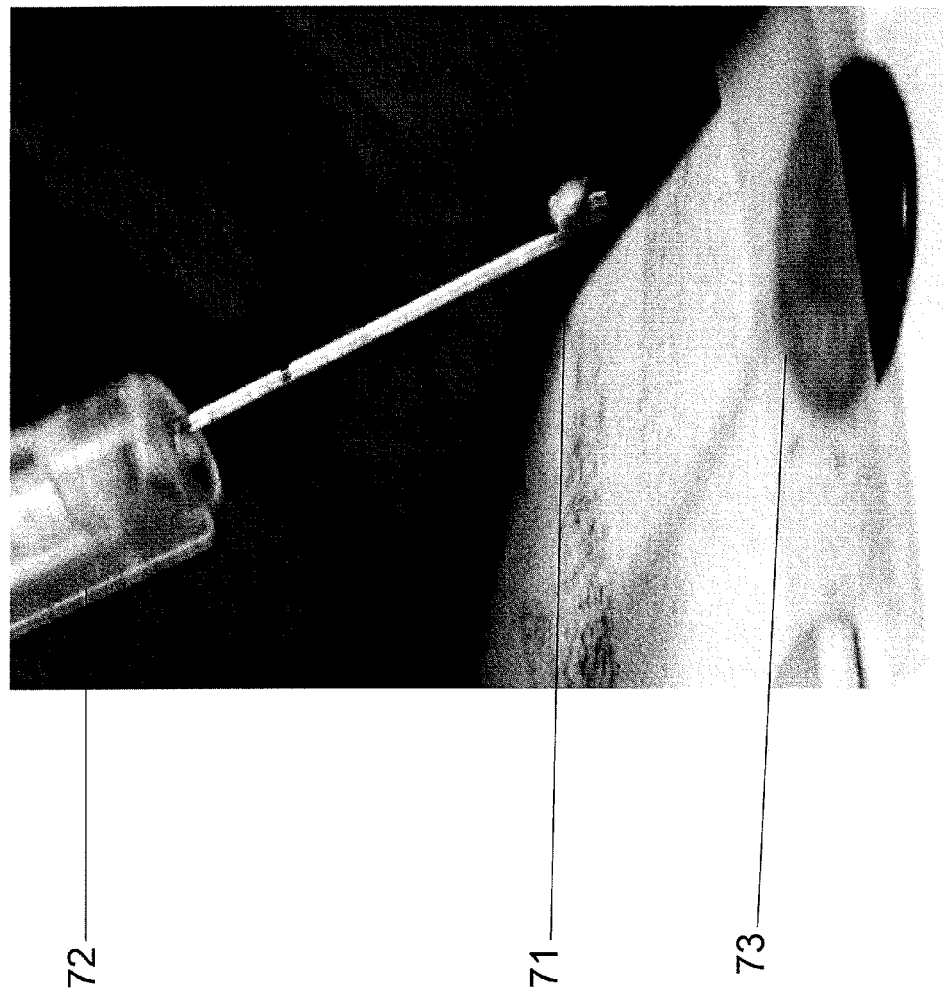
FIG. 9 is a perspective view photograph showing delivery of an aliquot of acetylcholine dissolved in water from a calibrated syringe (held in hand) to translucent tape to prepare an acetylcholine micro-patch in accordance with the present invention.

Two embodiments of micro-patches 2 in accordance with the present invention are shown in FIGS. 8 and 9. FIG. 8 shows the size of a nitroglycerin micro-patch 2 compared to a package 62 containing a full-size conventional patch. The rectangle shown here enables monitoring over an area greater than that covered by a standard stationary probe. For a stationary probe, a button-shaped micro-patch 2 typically is sufficient. FIG. 9 shows delivery of an aliquot of acetylcholine dissolved in water 71 from a calibrated syringe (held in hand) 72 for deposition on translucent double-stick tape 73 to prepare an acetylcholine micro-patch.

In addition to the various embodiments described above, it should be appreciated that multiple potential variations of micro-patches are contemplated for use in accordance with the present invention. FIGS. 10A to 10D shows how a small section 81 can be removed to create an opening 82 as a drug-free zone or for introduction of a second agent or to enable direct application of a monitoring probe 83. The multiple opportunities for evaluating drug interaction become evident when embedded microtubules 54 for infusion of agents and such an opening 82 are included in the same micro-patch 2. More particularly, FIG. 10A shows the opening 82 in the micro-patch 2. FIG. 10B shows how monitoring can be accomplished via the opening 82 through utilization of a monitoring probe 83 secured to the micro-patch 2 at the opening 82. FIGS. 10C and 10D show how drug delivery may be accomplished not only by simply applying drug via the opening 82 but also via microtubules 54 which enable delivery to the opening 82 as well as to other areas beneath the micro-patch 2.

In addition to the simple mechanisms for micro-patch application and adhesion and associated monitoring device interaction described above and illustrated in FIGS. 1, 2, 6, 7, and 10, in selected embodiments, secured advancement of a laser Doppler flowmetry probe or alternative monitoring device may be accomplished by one of several mechanisms of interaction and advancement. This process may offer the advantage of further limiting undesirable monitoring probe mobility and enables monitoring probe advancement so as to activate delivery of agent by the micro-patch 2. FIG. 11 shows a probe 1 and probe holder 5. The probe 1 includes threads 91 on an external surface thereof. The external threads 91a of the probe 1 are shaped and dimensioned for engagement with internal threads 91b formed along a cavity 95 of the probe holder 5. In this way the probe 1 may be adjusted relative to the probe holder 5 by simple rotation of the probe 1 relative to the probe holder 5.

FIG. 12 shows an alternate embodiment. As with the embodiment disclosed with reference to FIG. 11, the probe 1 includes threads on an external surface thereof. The threads of the probe 1 are shaped and dimensioned for engagement with internal threads formed along a cavity of the probe holder 5. The probe holder 5 is provided with a lower recess 96 including internal threads 97 on the inside of the lower recess 96 of the probe holder 5 for engagement with matched external threads 98 on a probe-to-study site coupler 92 upon which the micro-patch 2 is mounted for supporting the micro-patch 2 adjacent the study site. Advancement of the probe 1 by rotation of the probe holder 5 relative to the probe-to-study site couple 92 applies pressure to the micro-patch 2. While this may achieve drug delivery simply by increasing micro-patch 2 adherence to the study surface, it may also serve to advance drug-coated miniprojections when a micro-patch 2 such as those shown in FIGS. 5A and 5B is employed in accordance with the present invention.

In accordance with a preferred embodiment of the present invention, the present system has a baseline setting which fixes the probe without pressure on or just above the micro-patch and a second position which applies enough pressure to activate drug delivery. The pressure may remain for the duration of monitoring or one may return to the baseline position for subsequent monitoring. The process introduces another important feature for preferred embodiments in accordance with the present invention: if a multi-channel probe is used, it can be turned in calibrated increments so that multiple sites can be monitored without having to remove and replace the probe. While this contemplated technique may be accomplished using a variety of support structures, FIG. 13 presents a schematic of an exemplary support structure including a laser Doppler flowmetry probe 1 in a probe holder 5. The probe 1 is advanced and secured in position by luer-lock engagement of matched projections and grooves 100*a* and 100*b* herein respectively shown on the inner surface of lower recess 96 of the probe holder 5 and outer surface of the probe-to-study site coupler 92. This is accomplished by deliberate turning of the probe 1 and its probe holder 5. The micro-patch 2 is located in the coupler 92 and is pushed forward toward the study surface by probe 1 advancement via the threaded engagement of the probe 1 and probe holder 5 as discussed above with reference to FIG. 11.

FIG. 14 is a schematic showing a laser Doppler flowmetry probe 1 wherein the light guide fiber(s) is separated from the study surface by a spring 111 within the probe holder 5. The spring 111 resiliently supports the probe 1 within the probe holder 5 allowing for controlled movement of the probe 1 relative to the probe holder 5. After baseline readings are obtained with the micro-patch 2 lying gently on the study surface, the laser Doppler flowmetry probe 1 is advanced downwardly toward the study surface transiently compressing the spring 111 and increase adherence of the micro-patch to the study surface. In accordance with a preferred embodiment, it is contemplated the probe will be coupled to the micro-patch through the utilization of a probe-to-stud site coupler as discussed above with reference FIGS. 12 and 13.

Multiple alternatives for comparable engagement and disengagement previously have been described by the inventor, with respect to engaging needles and diaphragms, in U.S. Pat. No. 6,391,014, which is incorporated herein by reference. It is contemplated, these engagement and disengagement mechanisms may be employed within the spirit of the present invention. Although the basics of preferred techniques are disclosed above in accordance with a preferred embodiment of the present invention, those skilled in the art will appreciate a variety of mechanisms may be employed for facilitating movement of the probe.

In addition to embodiments where a single channel probe contacts the study surface or simply is separated from surface by the micro-patch and possibly adhesive, the present invention provides various embodiments that provide a persistent gap between the monitoring probe and the underlying tissue. Spatial heterogeneity under the probe may be mitigated by use of an integrating multichannel probe, a commercial version of which (from Perimed, Sweden) has seven closely packed channels that emit from a single source and return the signal to a singe detector. The use of such a probe in a fixed position reduces but does not eliminate the effect of spatial heterogeneity. In considering this problem the present invention adopts two modifications that are described below:

- A multi-channel probe 1 with independent channels confidentially customized to predetermined specifications. Like the commercially available integrating probe, this contains seven channels (other numbers of channels also acceptable). However, in contrast to the integrating probe, each channel is independently aligned with a detector. In the embodiment shown in FIG. 15, each channel 121 is also aligned with its own laser source. In the present photograph, three of the channels 121 are attached to a light source such that each of these independent channels 121 transmits light to the distal end of the probe 1, which is shown being mounted in a standard probe holder 5.

- Mounting the probe in a special holder that enables precisely repositioning the probe above the study site(s). FIG. 16 shows an inventive probe support assembly 131 for mounting a probe 1 (in this case a multichannel probe with a widened distal end) above the skin. The support assembly 131 is designed to enable consistent movements in fixed increments (e.g. 1 mm) so as to obtain new measurements without disturbing the alignment of the probe 1 with the skin or an underlying micro-patch 2. Movements are generated by a sliding bar 132 in horizontal and vertical directions in accordance with a visible grid 133. This new, movable, probe support assembly 131 was engineered so that the integrating probe 1 would be suspended a couple of millimeters above the study site 7 on the forehead, with the ability to be moved at fixed intervals in a two dimensional fashion. More specifically, it typically enables measurement of blood flow in a 1 cm×1 cm area on the forehead by obtaining multiple different readings in this area, with reading points distributed approximately 1 mm apart in a grid-like pattern. Using this probe support assembly 131 a significant decrease in the influence of spatial heterogeneity has been noted. Additionally, by rotating the probe 1 in approximately 30 degree increments, a second and third set of seven readings may be acquired without any probe 1 displacement or micro-patch 2 disturbance. This may be facilitated by use of tabs or related means to regulate the degree of rotation.

More particularly, and with referring once again to FIG. 16, the probe support assembly 131 includes four legs 134 extending downward for engagement with the subject, for example, the forehead 7 of the patient being treated. The engaging ends of the legs 134 are provided with adhesive pads 135 for secure attachment to the forehead. The legs 134 are threadingly engaged with the base structure 136 in a manner permitting relative adjustment. The slide arm 132 includes a coupling structure 137 for attachment of the probe 1 thereto in a manner such that the probe 1 is focused upon the forehead of an individual in a desired manner. As a result, one may move the slide arm 132 relative to the base structure 136 in a controlled and efficient manner. As shown with reference to FIG. 16, a micro-patch 2 is selectively placed under the probe 1 while it is held in this elevated assembly.

The size of the area that should be encompassed by a moving probe (or scanner) to capture areas of microvasculature that are close to as well as distant from the feeding arteriole, will depend on the region one is studying and should be based on evidence. This may be obtained by performing local biopsies to determine the distance between arteriolar-capillary networks or by mapping with a laser Doppler to determine the distance between peak values and then determining the distance that is required to ensure that the peak will be maintained in an acceptable number of patients (e.g., 95%, which may be obtained by 2 standard deviations). The inventor and his colleagues have compared laser Doppler readings to histological preparations from skin biopsies on ourselves and thereby gained an appreciation of the forearm microvasculature. [Braverman I M. Schechner J S. Silverman D G. Keh-Yen A. Topographic mapping of the cutaneous microcirculation using two outputs of laser-Doppler flowmetry: flux and the concentration of moving blood cells. Microvascular Research 44(1):33-48, 1992 July.] The application of mapping data will be limited by the size of the probe that can be comfortably and effectively placed and moved on the skin as well as on the acceptable size of micro-patch (so that only local effects are produced).

It is contemplated the benefits of a multichannel probe may be achieved with other configurations than the seven channel probe as shown. So long as cross-talk among fibers is minimal, they can be packed closely together and in different configurations. Individual probes also can be arrayed to sample an area of tissue. Spacing can be optimized to ensure maximum site coverage when the probe is rotated (as described above). It should be noted that, although the introduction of a multi-channel probe in accordance with the present invention is primarily for assessment as sites of transdermal application, the probe also is applicable to other types of challenges.

In its simplest form, the disclosed mechanism of monitoring perfusion does not require a computer, since one primarily is assessing increases in blood flow. However, it would be helpful to be able to delineate the time course of the response and to analyze potential changes in the oscillatory patterns of flow with computer-based algorithms. Embodiments which entail simultaneous recording of multiple inputs and/or frequent serial measurements obviously benefit from computerized acquisition (as described herein). Specifically, among the indices that can be monitored in accordance with the present invention are:

Absolute or percent changes in flow, including:
"drug phase/baseline" or
"(drug phase–baseline phase)/baseline".
Time course of changes in flow.
Changes in pulse wave associated with individual heartbeats.
Changes in oscillatory patterns, as the inventor and others have been shown to be indicative of cholinergic oscillatory and/or adrenergic control of the microvasculature. [Silverman D G, Stout R G: Distinction between atropine-sensitive control of microvascular and cardiac oscillatory activity. Microvasc Res 63:196-208, 2002; Silverman D G, Stout R G: Detection and characterization of cholinergic oscillatory control in peripheral microvasculature U.S. Pat. No. 7,367,941]
Changes in local vs. systemic values.

To date, evaluations have been performed of transdermal application of nicotine, nitroglycerin, estrogen and scopolamine (from existent large patches) as well as acetylcholine (micro-patch solution prepared by the inventor from acetylcholine powder) and phenylephrine (prepared by the inventor from existent solution). Since acetylcholine (as well as phenylephrine) had not previously been delivered transdermally, the efficacy thereof was tested with respect to doses, concentrations, vehicles and time-courses. This led to a preferred embodiment for delivery of these agents in a manner that enables drug delivery and concurrent laser Doppler monitoring.

A preferred embodiment of the present invention entails the use of acetylcholine, since this agent enables testing of the integrity of the microvasculature. The use of this agent in a micro-patch offers the unique advantages, including: a) acetylcholine is an endogenous vasodilator that is sensitive to disorders of the endothelium lining blood vessels; b) acetylcholine has a brief half-life, such that it is rapidly metabolized and hence, when administered as a micro-patch, has minimal systemic effects. These features have prompted the inventor to plan trials with succinylcholine, a drug that mimics the effect of acetylcholine at many receptors; it offers the added feature of prolonged residence and rapid metabolism since it is not metabolized at the tissues but by plasma cholinesterase in the blood. Trials with acetylcholine included multiple potential diluents with a range of hydrophilicity (vs hydrophobic) and translucency:

Ointments—oleaginous in nature
Creams—oil/water and water/oil emulsions
Gels—suspensions interpenetrated by a liquid Mixing was accomplished to achieve a final product that was smooth and free of abrasive particles. Based on trial and error testing, the inventor elected to pursue testing with acetylcholine chloride powder dissolved in water for placement on an adherent surface (e.g., clear tape). This led to a preferred embodiment of an acetylcholine micro-patch wherein acetylcholine solution is prepared by mixing 100-mg of acetylcholine chloride (Spectrum Chemical; New Brunswick, N.J.) with 0.6-mL high pressure liquid chromatography (HPLC) grade water to a final volume of 0.7-mL and molar concentration of 786.4 M. Then, as shown in FIG. 9, 0.02-mL (2.8 mg) of this concentrated acetylcholine solution 71 was spread on a translucent backing; originally a section of double-stick tape 73 but, more recently a commercially available double-stick clear disk (diameter 12.6 mm, area 124.7-mm$^2$) otherwise used for attaching two items but not for development of the inventive micro-patch. This dose is proportional to doses of MIOCHOL-E,™ (that is, a clinically available acetylcholine preparation that is used to produce papillary constriction (miosis) during cataract surgery) that had been tested in preliminary trials. However, the agent used for micro-patches can be superconcentrated compared to the solution used for intraocular injection—made possible because of the small delivery area.

The dry side of the acetylcholine "micro-patch" was adhered to the end of a laser Doppler flowmetry probe (a PF 5010 with Probe Model 407, Perimed, Sweden in accordance with a preferred embodiment) (see FIGS. 1 and 2). A sham drug micro-patch was made in the same way with 0.02-mL of HPLC-grade water instead of acetylcholine solution. Before micro-patch application, a Double-Stick Disc (3M Health Care, Neuss, Germany) (that is, the double-sided adhesive ring 6 discussed above) with an overall diameter of 38.1-mm and a central hole (or opening) diameter of 8.7-mm is placed at the site to be tested. The double-sided adhesive ring 6 serves as an adherent base onto which a monitor such as a laser Doppler flowmetry probe 1 is placed as well as to define the area (59.4-mm$^2$) for drug application. In addition to providing for targeted adherence, when placed between the micro-patch 2 and the study surface (as shown in FIG. 1) this further limits the area of drug delivery by providing a barrier to drug delivery from the outer regions of the micro-patch 2. As detailed below, this delivered as much as 10% of that used to constrict the pupil during cataract surgery Dose-response curve can be assessed with serial dilutions.

The following table compares the inventor's findings with transdermal application of acetylcholine to those with iontophoresis by us and other investigators in order to confirm that noniontophoretic transdermal delivery (introduced herein) is effective:

| Technique | Investigator | Approx Amount of Acetylcholine | Change in Blood Flow | Reference |
|---|---|---|---|---|
| Iontophoresis Forearm | Noon | 0.25 ml of 2% | 1000% inc | Br J Clin Pharmacol 1998;45:545-50 |

| Technique | Investigator | Approx Amount of Acetylcholine | Change in Blood Flow | Reference |
|---|---|---|---|---|
| Iontophoresis Forearm | Morris | 0.25 ml of 1% | 50-100% inc | Diabetologia 1995;38:1337-44 |
| Transdermal Forehead | Silverman | <0.25 ml of 1% | 50-250% inc | Data presented herein |

The creation of a nitroglycerin micro-patch so as to enable concurrent monitoring of an endothelium-dependent transdermal preparation (acetylcholine, described above) and an endothelium-independent vasodilator (nitroglycerin) is simpler than the creation of the acetylcholine micro-patch. As illustrated in FIG. 8, it entails the conversion of a full size patch (shown with reference to package 62) to a micro-patch 2 that is adhered to the skin and adapted for monitoring as per acetylcholine above. Inventive features include not only the application of this for monitoring the local circulation but the tailoring of the micro-patch to ensure effective delivery throughout the monitoring site while avoiding delivery of excess drug that might predispose to remote and/or systemic effects. For a single laser Doppler flowmetry probe, the nitroglycerin micro-patch may be obtained by using a standard hole-punch to cut a 6-mm diameter (28.3-mm$^2$ area) section of a full size 0.6 mg/hr MINITRAN™ nitroglycerin patch (3M, Minnesota). Alternatively, for applications where one wishes to move the laser Doppler flowmetry probe so as to encompass a larger area (as with the inventive assembly in FIG. 16), a small rectangle may be appropriate. Such patches are designed for homogeneous delivery of drug at a rate of 0.03-mg/hour per 100-mm$^2$ area of patch, such that the section used in the inventive micro-patch delivered at a rate of approximately 0.008-mg/hr. Although not currently available, higher concentrations of nitroglycerin may be used for micro-patches, pending dose response studies to confirm local efficacy and lack of systemic effects. The nitroglycerin micro-patch then is placed onto a double-sided adhesive ring for adherence to a laser Doppler flowmetry probe (see FIGS. 1 and 2) or it may be placed on the tissue under an elevated support assembly 131 or scanner (described below).

Prior to the customization of nitroglycerin according to the present invention, the inventor customized nicotine for this purpose. This entailed customization of a commercially available clear NICODERM patch, nicotine delivery patch, (with 0.83 mg of nicotine/cm$^2$). Again, higher concentrations may be used for a micro-patch; these are not currently available, since currently available nicotine patches delivery a fixed dose/cm$^2$ patch such that a higher systemic dose is obtained by using a larger patch.

The design of other transdermal preparations entailed processes similar to that for acetylcholine, nitroglycerin and nicotine. Transdermal phenylephrine was prepared by trial and error application of different concentrations and volumes of the drug as per acetylcholine. Micro-patches for nicotine, scopolamine and estrogen each was designed from a full-sized patch.

Testing of Micro-Patches in Accordance with the Present Invention:

Nicotine Micro-patches and Single Channel Laser Doppler Flowmetry Probe at a Single Study Site Most of the inventor's preliminary work was with customized modifications of a transparent nicotine patch. This was due to several reasons:

an FDA-approved nicotine transparent patch is available for clinical use;

systemic levels of nicotine are known to have significant cardiovascular effects, as recently confirmed by my use of nicotine lozenges [Mo C, Stout R G, Shelley K H, Tantawy H, Silverman D G: Acute microcirculatory effects of nicotine on non-smoking volunteers. Anesthesiology 2004; 101:A246J, prompting me to customize a nicotine micro-patch for isolating and testing local effects in the absence of systemic effects [Jablonka D, Silverman T J, Schonberger R B, Shahmohammadi K, Silverman D G: Nicotine induces vasodilation of the microvasculature independent of systemic sympathomimetic effect. ASA A1418:2006.]

The inventor's preliminary investigations with nicotine micro-patches (0.83 mg/cm$^2$) entailed customizing a section of the micro-patch so that it adhered to an area of skin that was sufficient to deliver drug to the area under a laser Doppler flowmetry probe and that enabled attachment of the laser Doppler flowmetry probe to an upper surface of the micro-patch. This led to the following findings.

Figure 17:
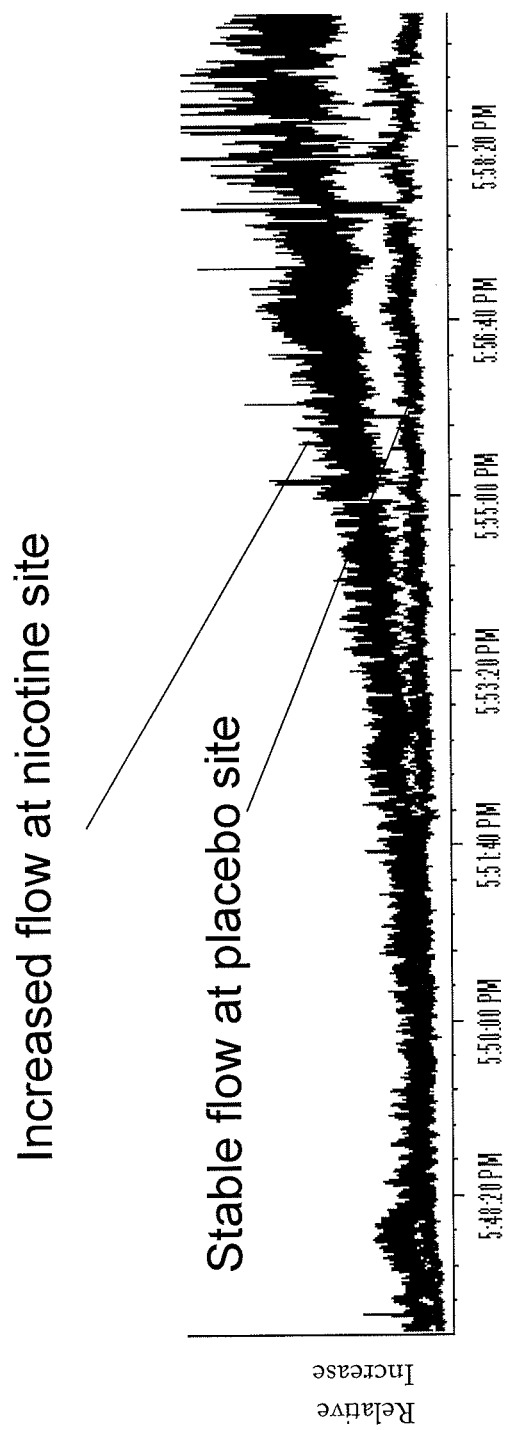
FIG. 17 shows continuous flow readings obtained with laser Doppler flowmetry probes placed at a site of a nicotine micro-patch (upper) and a placebo gel (lower) on the forehead in accordance with the present invention. x-axis=time in minutes; y-axis=voltage output (relative flow above baseline, values not shown). Between 5 and 15 minutes after application of the nicotine micro-patch, flow at the nicotine site increased progressively to approximately 300% of baseline, providing heretofore unknown information about the direct effect of nicotine on the microvasculature in this region (as opposed to information obtained after systemic administration).

As shown with reference to FIG. 17, transdermal application of nicotine at the cholinergically rich forehead (i.e., a region rich in acetylcholine receptors) causes a 2-5-fold increase in local blood flow within 30 min. A button-sized translucent nicotine micro-patch caused a 388.4% increase at the active site and a 2.9% increase at the placebo site when applied to the forehead of seven healthy subjects (two-tailed=0.012 for difference between nicotine and placebo sites). The difference likewise is seen in results generated by a laser Doppler scanner (discussed below).

When drug delivery was limited to the micro-patch, the increase in flow was limited to skin at or adjacent to the site of micro-patch application; no response was evident at a remote site or in systemic indices (e.g., heart rate, blood pressure, flow at other sites).

Figure 18:
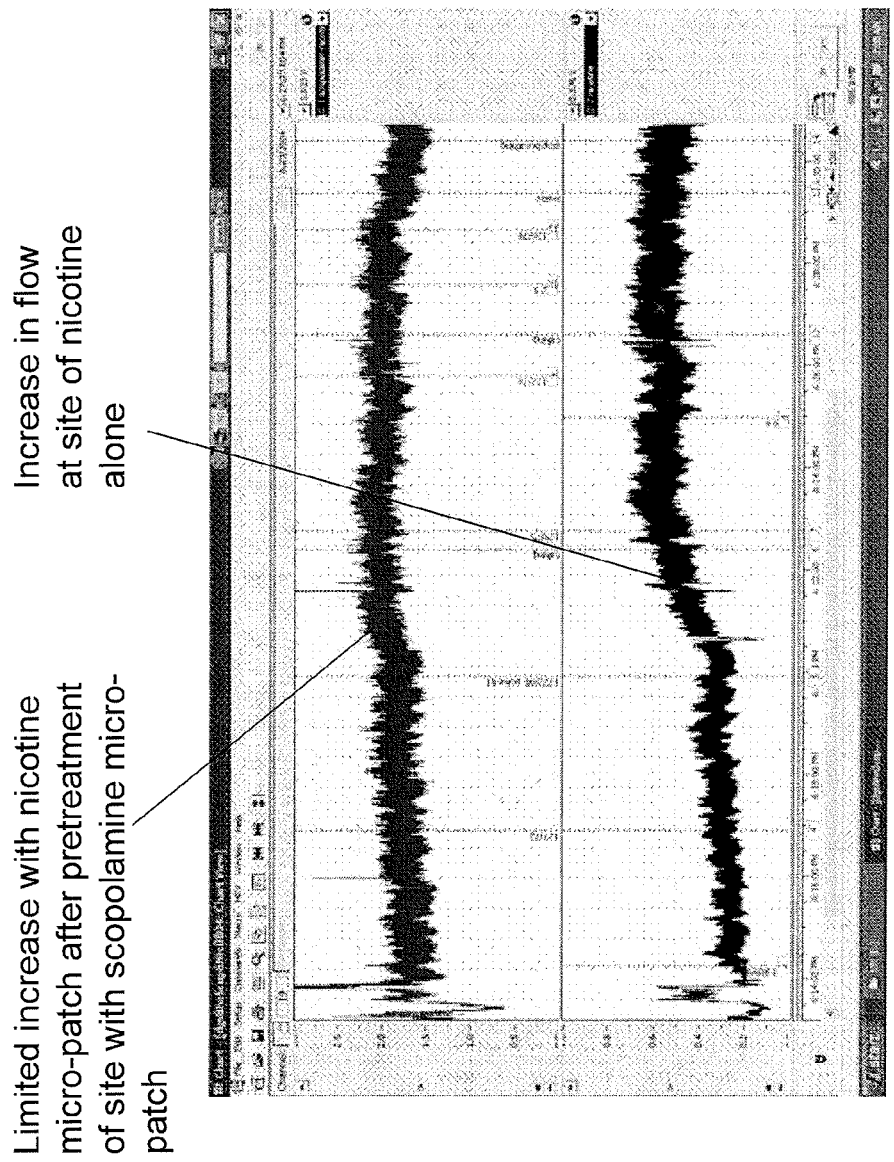
FIG. 18 shows tracings from two laser Doppler flowmetry probes on the forehead in accordance with the present invention, wherein the application of scopolamine before nicotine blunted the increase in perfusion seen with nicotine alone.

As shown in FIG. 18, embodiments of the inventive micro-patch technology provide the ability to monitor the effects of two agents applied concurrently. Here, the addition of scopolamine (top tracing) blunted the vasodilatory response induced by nicotine alone (lower tracing).

Hence, this preliminary work identified the efficacy and safety (lack of remote effects) of micro-patch technology in accordance with the present invention and enabled attainment of information about the microcirculatory effects of nicotine that heretofore had not been appreciated [Mo C, Stout R G, Shelley K H, Tantawy H, Silverman D G: Acute microcirculatory effects of nicotine in non-smoking volunteers. Anesthesiology 2004; 101:A246.]. Alternatively, the combination of a transdermal medication with a systemic medication enables what may be referred to as "dual platform" testing.

The inventor's initial assessments with the nicotine patch also included assessments of light transmission properties and how they are impacted by micro-patches:

The laser Doppler signal was only slightly (and consistently) diminished by approximately 20% by placing a transparent covering (e.g., TEGADERM®) between the end of the monitoring laser Doppler flowmetry probe and the skin. This provided evidence that the laser Doppler flowmetry probe could sufficiently detect a signal through a clear micro-patch.

The laser Doppler signal was diminished immediately upon placing a clear NICODERM® micro-patch on the skin beneath the laser Doppler flowmetry probe, but the signal remained readily detectable. This attenuation was attributable to the impeded light path caused by the plastic backing (an impermeable plastic sheet that is thicker than a TEGADERM®) and the drug (nicotine)/inactive vehicle layer (—one manufacturer reported the contents to include acrylate adhesive, aluminized polyester, cellulose paper, and methacrylic acid copolymer). The consistency over time of the impedance of light transmission in the absence of a subsequent drug effect was tested by placing a clear NICODERM® micro-patch upside down (with the impermeable backing preventing delivery of drug). The equivalent decline in light transmission persisted for a 45-min testing period. Hence, it would not distort assessment of drug effect on perfusion.

Note—the clear NICODERM® patch that is commercially available was designed for cosmetic reasons, not to facilitate monitoring. It has writing on most of its surface, which impedes light transmission, and it is not of a desirable size for local testing. In accordance with the present invention, sections without writing were selectively punched out to create a translucent "micro-patch" for use in studies.

Nitroglycerin and Acetylcholine Micro-patches and Single-Channel Laser Doppler Probe at a Single Study Site.

The inventor has conducted testing of, and with, micro-patches in accordance with the present invention. In particular, micro-patches with two agents that more commonly are used to interrogate the microvasculature, acetylcholine and nitroglycerin, have been introduced. These were applied in the following preliminary clinical studies, with the approval of the Human Investigation Committee of Yale University School of Medicine. Three studies are summarized below.

Study A: Clinical Application of Acetylcholine and Nitroglycerin Micro-Patches

This relates the responses to acetylcholine and nitroglycerin micro-patch preparations. Testing is reported in detail in Schonberger R B, Worden W S, Shahmohammadi K, Menn K, Silverman T J, Stout R G, Shelley K H, Silverman D G: Topical non-iontophoretic application of acetylcholine and nitroglycerin via a translucent patch: a new means for assessing microvascular reactivity. Yale J Biol Med 78:229-235, 2006, which is incorporated herein by reference.

Figure 19:
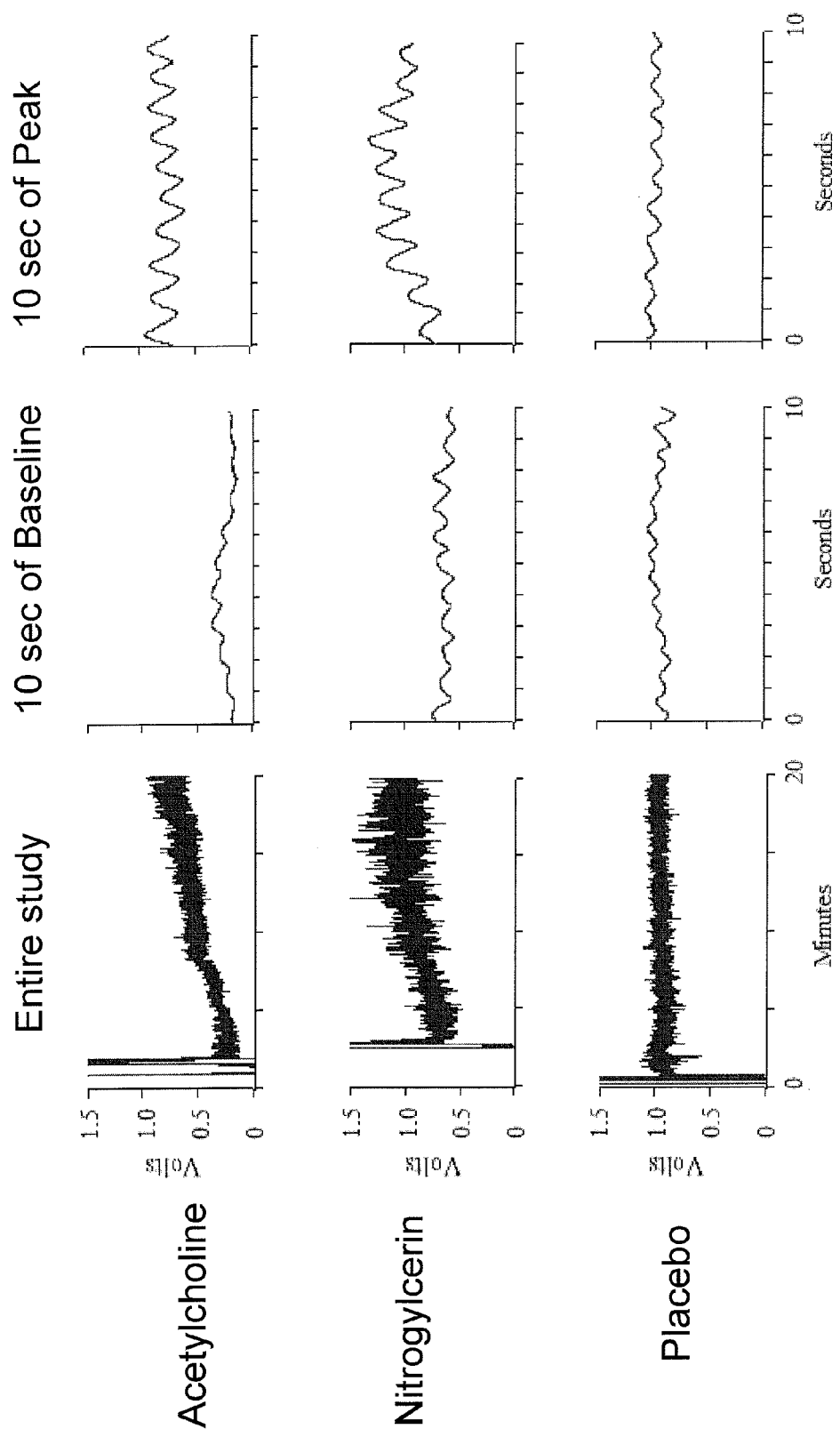
FIG. 19 is a series of graphs presenting representative data (laser Doppler values, in volts) from three laser Doppler flowmetry probes atop micro-patches on a healthy subject illustrating readings at the site of the inventive nonionto-phoretic micro-patch acetylcholine solution (top row), at the site of a nitroglycerin micro-patch (middle row), and at a placebo site (bottom row) in accordance with micro-patches introduced in the present invention. The entire 20 minute study period is shown in the left hand column; 10 seconds at baseline and 10 seconds during the plateau phase are shown in the middle and right hand columns, respectively. Prompt increases in blood flow at the sites of transdermal acetylcholine and transdermal nitroglycerin application are seen. This is manifested not only by an increase in mean flow but also in the amplitude of each pulsation at the cardiac frequency.
Figure 20:
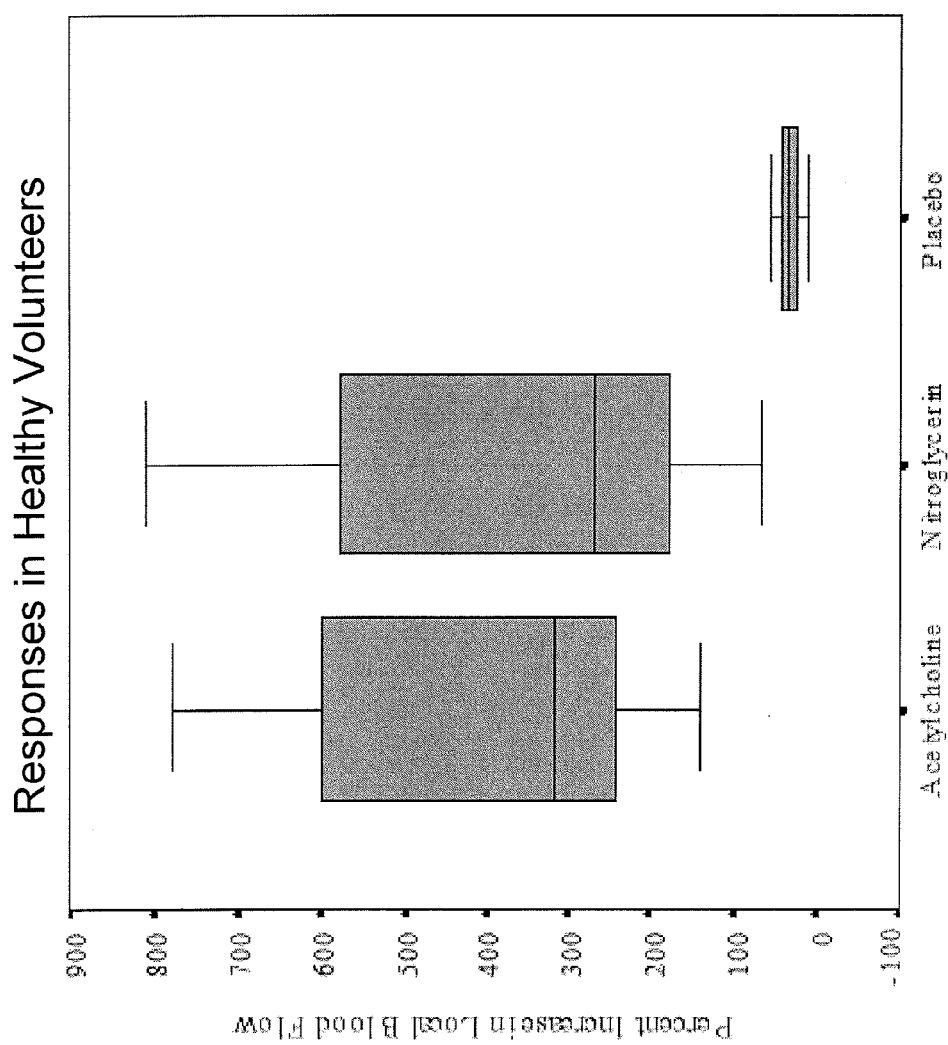
FIG. 20 shows boxplots summarizing the response to acetylcholine, nitroglycerin and placebo micro-patches in 10 healthy volunteers obtained in accordance with the present invention. Data are presented as mean percent increase in laser Doppler flowmetry voltage with 95% confidence intervals (CI).
Figure 21:
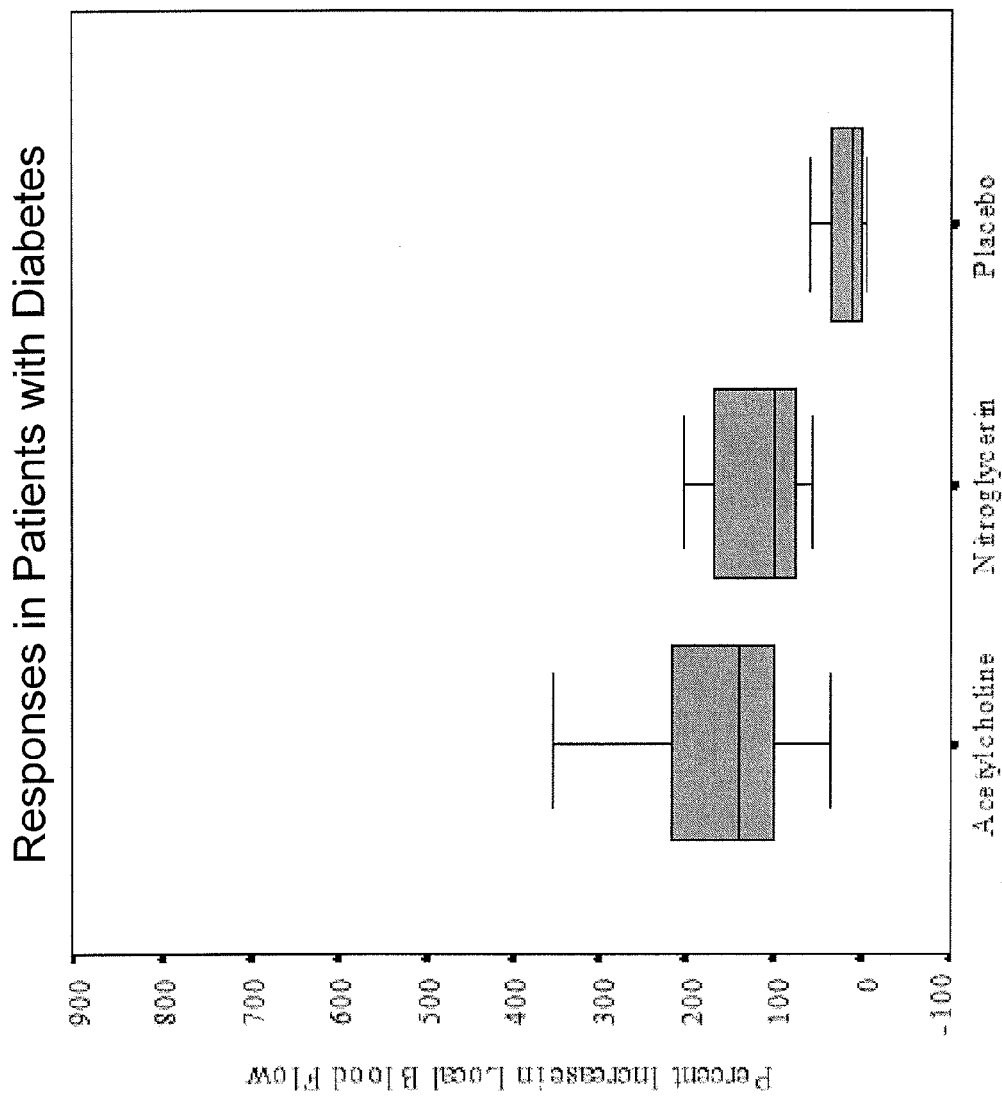
FIG. 21 shows boxplots summarizing reduced response of standard laser Doppler flowmetry to acetylcholine, nitroglycerin and placebo micro-patches in 10 patients with diabetes. Data are presented as mean percent increase in voltage with 95% confidence intervals (CI).

Ten healthy volunteers and 10 patients with diabetes were recruited for laser Doppler flowmetry measurements of forehead perfusion at sites of transdermal application of acetylcholine, nitroglycerin, and placebo. This enabled generation of tentative cutoffs in a preliminary derivation data set which, after further refinement, will be tested in validation data sets. With the doses used, both nitroglycerin and acetylcholine induced significantly greater increases in flow in healthy volunteers than in patients with retinopathy as a consequence of diabetes. Typical tracings are shown in FIG. 19; the different responses in healthy volunteers and patients are summarized in the boxplots of FIGS. 20 and 21, respectively.

Methods:

For each session, subjects lay on a bed in a semi-recumbent position in a temperature-controlled room (24±1° C.). A three-lead electrocardiogram and a non-invasive brachial artery blood pressure cuff were applied. The three laser Doppler flowmetry probes with customized acetylcholine, nitroglycerin, and placebo micro-patches (as described above) attached were adhered onto the three double-stick discs on the forehead so as to enable undisturbed monitoring and drug delivery. Laser Doppler flowmetry monitoring was performed continuously at each site until a vasodilatory plateau was maintained for >3 minutes or for a maximum of 20 minutes. Data were collected at a rate of 1000 Hz using Chart for Windows (ADInstruments, Colorado Springs, Colo.).

The local microvascular effects of transdermal acetylcholine and nitroglycerin were first tested in 10 healthy volunteers (7 males, 3 females; mean age 36.1, range 19 to 56 years) without vascular disease or diabetes. The effects also were tested in 10 diabetic subjects (3 males, 7 females; mean age 56.5, range 40 to 73 years) recruited in the retina clinic of the Yale Eye Center. (This preliminary assessment did not match subjects for comorbidities and medications, nor impose dietary restrictions.)

An investigator blinded to the status of the subject and to the nature of the study site assessed the laser Doppler tracing at each study site. The pre-study trials had indicated that, within 10 seconds of laser Doppler flowmetry probe application, a steady baseline interval was consistently obtainable and that a progressive drug-induced rise in flow with both acetylcholine (top tracing in FIG. 19) and nitroglycerin (middle tracing in FIG. 19) was noted to begin no sooner than 30 seconds after probe application. This enabled a 20 second baseline period to be obtained, without the need to remove the laser Doppler flowmetry probe for subsequent drug application. This baseline period may be prolonged by means of delaying drug delivery such as agent encapsulation and/or introducing an inactive layer (see FIGS. 3-5) or by obtaining baseline readings before drug delivery (as per means for integrated delivery and monitoring shown in FIGS. 7 and 10, and for adaptive monitoring in FIGS. 12, 13, 14, and 16). Each laser Doppler flowmetry probe remained in place for up to 20 minutes. The drug-induced increase in flow in the present study was determined by comparing the mean during the lowest 10-second interval during the baseline period at the acetylcholine, nitroglycerin, and placebo (bottom tracing) sites with the mean during the maximum 10-second interval after a plateau was reached at the acetylcholine, nitroglycerin, and placebo sites. The effects of the single dose of acetylcholine was compared to the single dose of nitroglycerin in the healthy volunteers, with the differences analyzed using Wilcoxon Signed Rank Test (WSRT). Second, a preliminary assessment of the response in the healthy volunteers versus the 10 diabetic patients (who were older and had varied medical conditions and medications) were compared using the Mann-Whitney U Test (MWUT).

Results:

Acetylcholine and nitroglycerin, but not placebo, induced a marked rise in laser Doppler flowmetry voltage within two minutes of drug application in each healthy volunteer. This was evident not only with respect to mean flow, but also with respect to the amplitude of the pulsation coincident with each heart beat (see FIG. 19). Blood flow at the treatment sites remained elevated for the duration of the study session. Readings increased by 306% (245%-566%) and 36% (26%-46%), respectively, at the acetylcholine and placebo sites (p=0.005 by WSRT); and they increased by 265% (179%-550%) at the nitroglycerin site (p=0.005 by WSRT versus placebo; p=NS versus acetylcholine) (see FIG. 20). The absence of a systemic response was confirmed by the lack of dilation at the placebo site and by the lack of significant change in systemic blood pressure and heart rate.

The vasodilatory responses to acetylcholine and nitroglycerin in diabetics were significantly greater than to placebo (see FIG. 21), but much less than in healthy volunteers. Mean percent increases in blood flow were 156% (91%-221%) and 116% (79%-153%), respectively, at the acetylcholine and nitroglycerin sites, vs. 21% (CI 4-37%) at the placebo site (p=0.005 by WSRT for placebo versus each active site). The responses of the diabetic patients to acetylcholine and nitroglycerin did not differ significantly from each other (p=NS by WSRT). The diabetics' responses at each active site were significantly impaired relative to healthy subjects (p<0.001 and p=0.009, for acetylcholine and nitroglycerin respectively, by MWUT).

Comparison between FIGS. 17 and 19 shows that there is potential to regulate the rate of uptake based upon the nature of active agent and/or vehicle and/or patch construction: the onset of the different agents and their comparative effects on mean flow vs. the change in systolic amplitude (pulse height) and mean flow differed among the acetylcholine, nitroglycerin and nicotine micro-patches. The figures also illustrate that the stored data enables determination not only of mean flow, but also the impact of an agent on components of the pulse wave with each heart beat, including peak (at systole), trough (at diastole), peak to trough, trough-to-peak upslope, and peak-to-trough downslope. Capture of the waveforms by sampling at a sufficient frequency ($\geq$200 Hz in the present studies so as to also enable analysis of the electrocardiogram, but slower rates should be sufficient for laser Doppler flowmetry alone) to enable characterization of oscillatory activity and how it changed by the micro-patch. FIG. 19 shows that oscillatory activity appears greater at the acetylcholine site during baseline and at the nitroglycerin site during micro-patch application. Admittedly, this constitutes too little data to draw conclusions. I have provided the details for such assessments and their significance in papers and an approved patent. [Silverman D G, Stout R G: Distinction between atropine-sensitive control of microvascular and cardiac oscillatory activity. Microvasc Res 63:196-208, 2002; Silverman D G, Stout R G, Lee F A, Ferneini E M: Detection and characterization of cholinergic oscillatory control in the forehead microvasculature in response to systemic alpha-agonist infusion in healthy volunteers. Microvasc Res 2001; 61:144-7; U.S. patent application Ser. No. 10/437,452 to David G. Silverman et al., entitled "Detection and Characterization of Cholinergic Oscillatory Control in Peripheral Microvasculature and Other Cardiovascular Signals", which is incorporated herein by reference. Additionally, comparisons may vary, with respect to within-patch comparison to baseline as well as to a reference or placebo site, or as shown above for the comparison between acetylcholine and nitroglycerin, among agents.

Study B: Modifications of Monitoring Technique with the Laser Doppler Flowmetry Probe to Address Spatial Heterogeneity This introduced and evaluated new mechanisms for overcoming the intrasubject variability caused by spatial heterogeneity among neighboring sites of a measure of perfusion such as laser Doppler flowmetry. It showed that monitoring multiple data points in a tightly controlled measurement area can allow for a more accurate and reproducible determination of microvascular responsiveness in a given subject. The study consisted of two parts (approved my institution's Human Investigation Committee). The findings were presented by the inventor's team: Nissen A, Rose M, Schonberger R B, Silverman T J, Silverman D G: Consistency of laser Doppler assessments of vasoreactivity. American Society of Anesthesiologists 2A244:2006, which is incorporated herein by reference.

In part 1 (n=6 with "standard laser Doppler technique"), the effect of transdermal nitroglycerin on forehead blood flow was assessed through a portion of a translucent nitroglycerin patch with a standard 0.25-mm laser Doppler flowmetry probe (PF 5010, Perimed, Sweden) at a single site. Part 2 (n=4) was designed to minimize the impact of spatial heterogeneity by assessing the effect of transdermal nitroglycerin with the configuration shown in FIG. 16 at a fixed distance above the bridge of the nose. As detailed above, a seven-cable integrating laser Doppler flowmetry probe (probe 413, PeriMed, Sweden) 1 was mounted in a special support assembly 131 above the study site so that it could be moved in 1.25-mm increments in accordance with the present invention to obtain 16 measurements within a 1-cm$^2$ grid; the mean of the sixteen measurements was recorded. Each part consisted of two sessions at least 24 hours apart, wherein the nitroglycerin-induced increase in perfusion (from baseline) was recorded with the given probe after a vasodilatory plateau was reached within 10-20 minutes after drug application. Within each subject, the increase induced by nitroglycerin on the two days was compared; the Day 1 vs. Day 2 variation in response was expressed as % difference.

The findings illustrated the ability of both mechanisms to delineate changes induced by an inventive micro-patch. However, the techniques differed with respect to day-to-day variability. In Part 1 (standard probe), the mean day-to-day % difference averaged 100% (with a range of 20% to 300%) between the two study days. Conversely, in part 2 (integrating/multisite technique), the mean day-to-day % difference averaged only 20% (with a range of 10% to 30%) between the two study days. The relative day-to-day % difference with the integrating technique was significantly less than with the traditional probe (p=0.04; Mann-Whitney-U Test)

Figure 15:
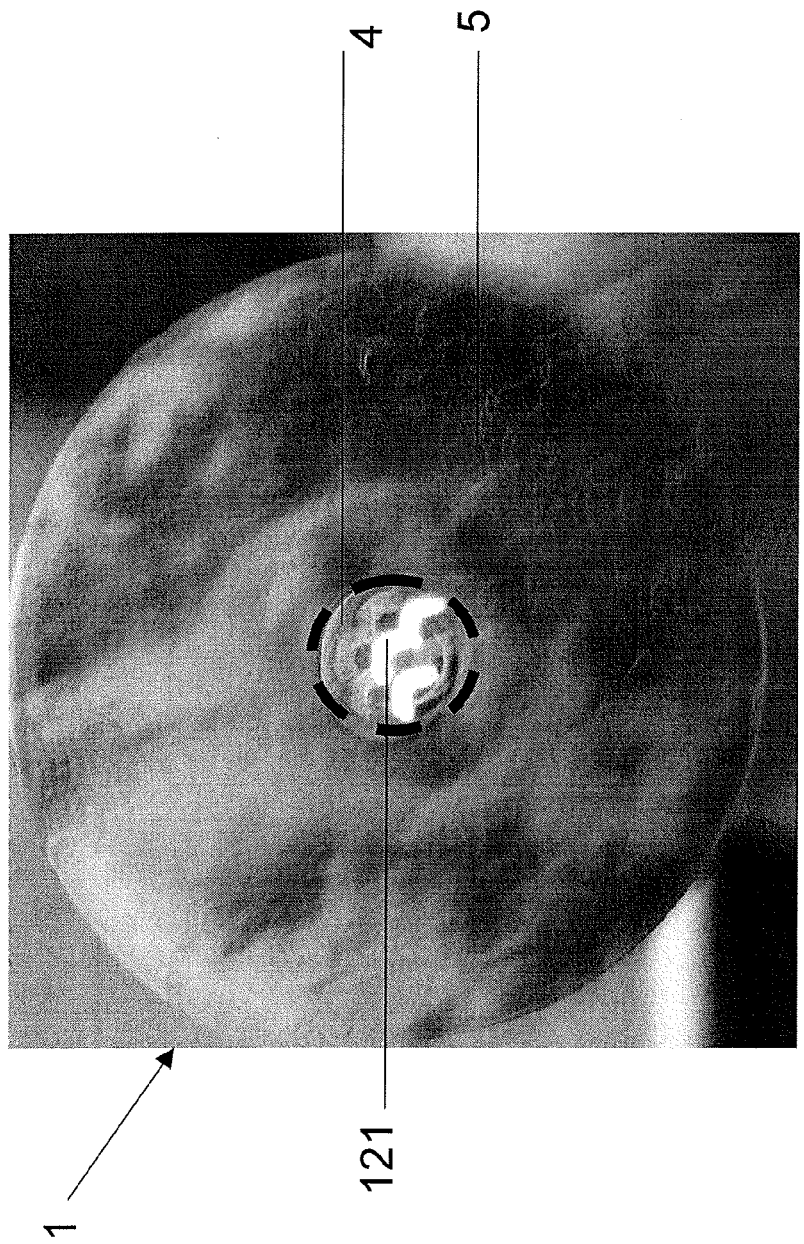
FIG. 15 is a bottom plan view showing a multi-channel probe. Like the commercially available integrating probe, this probe contains seven channels (other numbers of channels also acceptable). However, and in contrast to commercially available integrating probes, each channel is independently aligned with a detector. In the present embodiment, each channel is also aligned with its own laser source. In the view shown with reference to FIG. 15, three of the channels are attached to a light source.

To varying degrees, the increased consistency in the context of potential spatial heterogeneity reported above can be achieved in a variety of ways, including:

Use of the aforementioned integrating probe at a single location, with the option to mark the skin;

Use of a single channel probe at multiple neighboring sites;

Use of a multichannel probe (where the signal from each channel is assessed separately; FIG. 15) at one or more sites, with or without rotation at said site(s).

Figure 10:
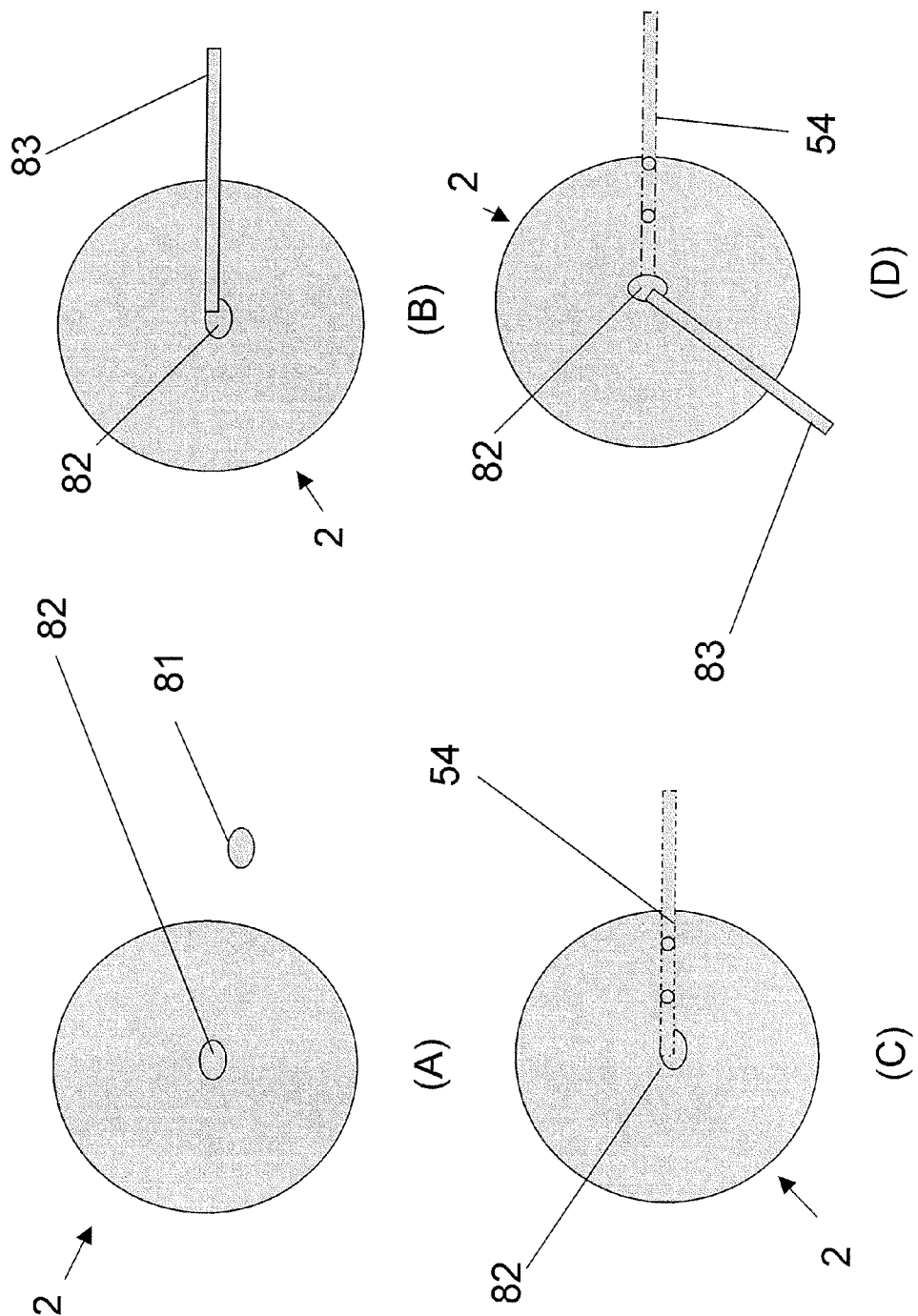
FIGS. 10A-10D is a series of schematics of alternate embodiments showing micro-patches provided with an opening in the center of the micro-patch. While typically not necessary in view of the aforementioned embodiments, this provides an alternative for delivery of drug (especially a second drug) and enables monitoring without an intervening patch.
Figure 11:
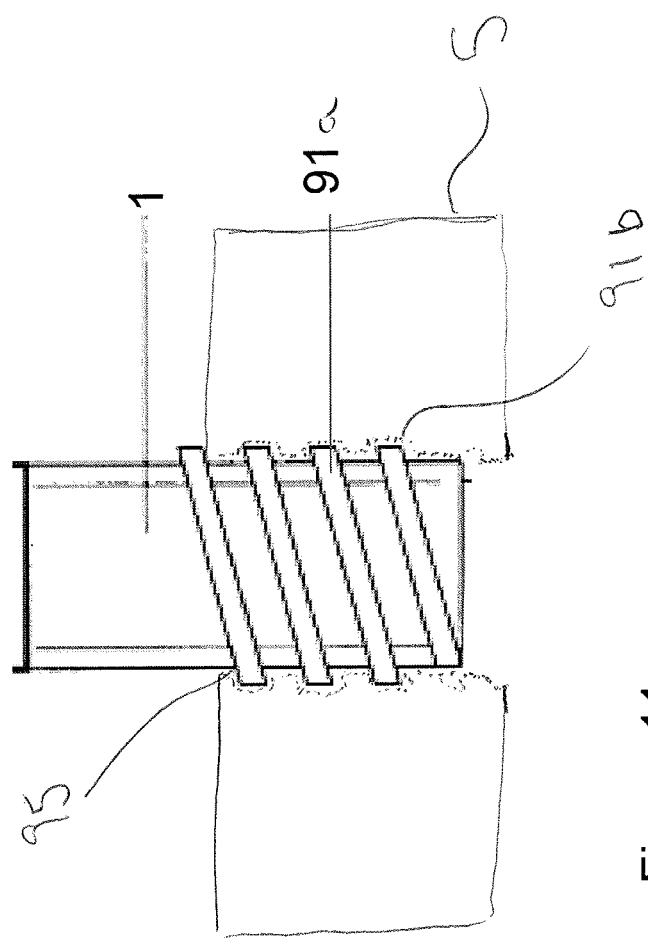
FIG. 11 is a plan view of a schematic showing a laser Doppler flowmetry probe and probe holder with threading for advancing the laser Doppler flowmetry probe, or alternative monitoring device, within a holder adherent to skin by a screwing mechanism for threaded engagement. This arrangement and modifications such as those shown in FIGS. 12, 13 and 14 enable probe advancement so as to activate delivery of agent by the micro-patch (after baseline), and/or enable deliberate rotation of a probe so as to sample multiple sites without having to remove and replace the probe (especially if a probe with multiple channels is used) and, when desired, may further limit probe mobility.

Means for enabling persist placement of monitors: e.g., micro-patches with microtubules 54 as shown in FIGS. 7 and 10; micro-patches with an area at one end 53 for anchoring to the skin as shown in FIGS. 7 and 8;

Study C: Additional Applications

This illustrates the use to acetylcholine and nitroglycerin micro-patches and the integrated probe technology to evaluate the effect of a potential insult to the microvasculature. My team found that the ratio of endothelium-dependent to endothelium-independent vasodilation appears to be greater after a normal meal than after a fat-laden meal (which is an example of a dual platform. [Nissen A F, Calo L, Silverman T J, Shelley K H, Silverman D G: Sensitivity of acetylcholine and nitroglycerin-induced vasodilation to endothelial impairment. Anesthesiology 2007; 107:A291.]

Methods:

With Institutional Review Board approval, six healthy volunteers (3 male, 3 female) were recruited for a two-session study in which they randomly ate a fat-laden, 900 calorie meal or a fat-free meal of comparable calories. Two hours later, subjects underwent application of acetylcholine and nitroglycerin micro-patches. As described above, the former was prepared by mixing 100 mg of solid acetylcholine with 6 ml of sterile water. From this solution (concentration of 14.3 mg/ml) we used an aliquot of just under 0.14 ml (less than 10% of the standard 20 mg dose injected into the eye during cataract surgery). The latter consisted of a 1.4 cm×1.4 cm translucent square (cut from a full-sized nitroglycerin patch) for delivery of 0.008 mg/hr of nitroglycerin to the study site. Before each patch application, seven sites of the forehead were monitored with a commercially available integrating laser Doppler flowmetry probe that averages the output from several closely packed light-transmitting channels (to partially overcome spatial heterogeneity). At 10 minutes after patch application, readings were repeated. Changes were analyzed using paired t-test.

Results:

Although the response to acetylcholine was still present after the fat-laden meal, the relative increase induced by acetylcholine compared to that induced by nitroglycerin was significantly less than after the nonfat meal. The nitroglycerin/acetylcholine ratio was 1.31 and 0.94, respectively after the fat and nonfat meals (p=0.036). The prolonged application of the inventive micro-patches and customized means of inventive monitoring through the micro-patch indicated that, in response to a challenge which compromises endothelial function, the relative vasodilatory effect of acetylcholine was reduced compared to that of nitroglycerin. This is but one example of the potential applications of the inventive technology to address clinically relevant issues.

Figure 26:
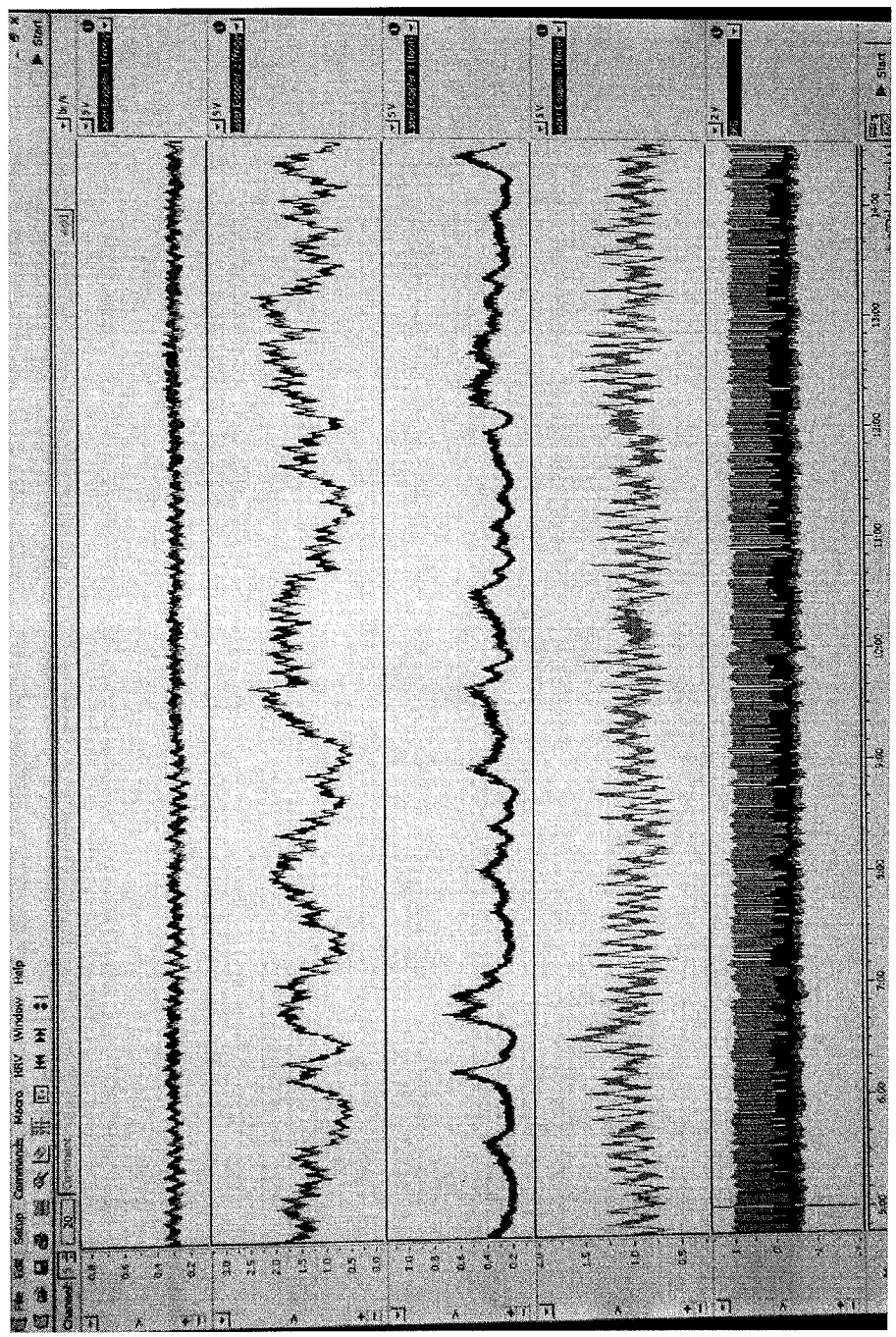
FIG. 26 is a snapshot of a screen showing continuous tracings from multiple channels; time on x-axis, magnitude of each signal on y-axis. It illustrates four laser Doppler signals (from four different sites) and the electrocardiographic tracing so as to monitor changes in heart rate, heart rate variability and even the morphology of the electrocardiogram waveform.

As noted above, a major advantage of the micro-patch is its induction of changes in the microvasculature at the study site without remote or systemic impact. This can be confirmed by monitoring at remote sites or by monitoring systemic indices such as a heart rate or blood pressure. This may be accomplished with a coordinated data acquisition system such as that shown in FIG. 26. This shows real-time input from four laser Doppler flowmetry probes (top four rows) and a continuous electrocardiogram tracing (bottom row). In addition to confirming the intended lack of remote or systemic responses, such a system can be used to identify such responses when they are being sought (as would be the case if one were performing dose-response studies and/or wishing to confirm that a given preparation is being absorbed even if it did not induce changes at the study site). The acquired data are transferable to spread sheets for analysis of individual channels and comparative analyses among channels.

Alternative Micro-Patch Embodiments

It is contemplated embodiments of the drug-containing micro-patch could be an individualized combination of drug and adhesive (as described above for acetylcholine), a punchout/cutout from a larger patch (as described for nicotine and nitroglycerin), mass-produced button-sized units, or a peel-away unit from a larger strip. Alternatively, especially when monitoring does not touch the study site, the inventive "micro-patch" could take the form of precise aliquots of a "micro-applicant" that may consist of a thin layer of the preparation in accordance with the inventive concentrations and delivery described above, in a translucent vehicle without a backing. Not only would the unique micro-patching dosing and concentration and nonintrusive delivery introduced herein apply in such settings, but also the mechanisms for assessing the effects on the local microvasculature (e.g., availability of placebo, applicability to multiple sites, monitoring techniques, assessment of data). Nonetheless, preparation of a micro-patch with backing increases consistency of dosing and rate of delivery, is more amenable to applying layers (such as the inactive layer 32 and agent layer 34 in FIG. 3) and decreases the risk of contamination of other sites or the individual applying the drug.

As an alternative to the small micro-patch, a full-sized patch could have all but the monitoring site(s) covered with a custom-fitted impermeable shield. The number of sites and the size of each site would be determined by how much of the shield is removed. However, this involves the application of the patch to a larger area, with the potential for accidental overdose. Alternatively, large patches could be prepared with predetermined active "micro-patch" regions.

If one felt it necessary to eliminate the potential impact of the ointment or gel on the ability of the laser Doppler to detect a signal, the invention can be modified to include a very small drug-free zone underneath the planned site of probe placement. One means to do this is as follows: when the micro-patch is being coated with drug, a small piece of tape would be placed over the desired drug-free zone so that it did not acquire any drug. The tape could then be removed before applying the micro-patch to the skin; this would be the site at which the laser Doppler flowmetry probe (or alternative monitoring technique) would be applied to view the skin. Preliminary trials indicate that the spread of drug in the local tissues is sufficient to achieve an effect at an immediately adjacent site which is circumscribed by the micro-patch and/or vehicle. Specifically, data from the study shown in FIG. 18 indicate that the local effects of nicotine with this configuration (i.e., nicotine-induced increase in blood flow beyond the bounds of the nicotine micro-patch) and of scopolamine (i.e., this caused inhibition of the effects of nicotine applied through a hole in a scopolamine micro-patch) showed that effective delivery could be achieved from adjacent areas to the small drug-free region of the micro-patch. If a hole (or opening) 82 such as that in FIG. 10 is used, it should be as narrow as possible while still ensuring support of the monitoring probe and/or allowing for administration of additional agent. Whereas a 10 mm diameter opening was effective for the combined assessment of nicotine and scopolamine (FIG. 18) settings, the precise dimensions would depend on the diffusibility of the specific agent(s).

Alternative Embodiments for Monitoring and Additional Micro-Patch Studies

Monitoring the responses of the local microvasculature may entail a wide range of techniques, including laser Doppler flowmetry via a monitoring probe, laser Doppler scanning, laser speckle imaging (discussed below), surface reflectance photoplethysmography, angiography, and thermometry.

To date, the micro-patch embodiments have been tested primarily with laser Doppler flowmetry probes and a laser Doppler scanner. Initial studies with a laser Doppler flowmetry probe and the inventive micro-patch were performed with a standard 1 mm diameter probe (described above). Traditionally, measurements have been made with a single laser Doppler flowmetry probe at a single site. The temporal variability that occurs with each heart beat (high at systole, low at diastole) and over the course of periodic oscillations (typically in the range of 1 every 5-20 seconds) can be overcome by monitoring at a single site for a sufficient period of time. The nature of the oscillatory activity also may provide valuable information as noted in a commonly owned and copending patent application (which does not address micro-patch technology); that is, U.S. patent application Ser. No. 10/437,452 to David G. Silverman et al., entitled "Detection and Characterization of Cholinergic Oscillatory Control in Peripheral Microvasculature and Other Cardiovascular Signals", which is incorporated herein by reference.

Consistent with other investigators, my colleagues and I encountered intra-subject variability as a consequence of spatial variability at the microvascular level. In 1992, I co-authored a study that delineated the spatial heterogeneity of the microvasculature, wherein 1×1 mm monitoring sites with a 10×10 mm area had areas ranging from virtually no capillaries to a rich network containing many capillaries as well as an arteriole that was oriented horizontally (and thereby generate a maximal reading). [Braverman T M. Schechner J S. Silverman D G. Keh-Yen A. Topographic mapping of the cutaneous microcirculation using two outputs of laser-Doppler flowmetry: flux and the concentration of moving blood cells. Microvascular Research 44(1):33-48, 1992 July.] The variability is such that taking the laser Doppler flowmetry probe off and replacing it may result in a significant change in laser Doppler values and, as I have shown in my trials with the micro-patch, in the measured response to a vasoactive drug. That is, one can get greatly different blood flow measurements depending on where the laser Doppler flowmetry probe is attached even within a fairly confined area on, for example, the forehead. This makes it harder to accurately analyze the effect of interventions done on different days aimed at altering blood flow, as one does not know whether the change in flow seen is secondary to the intervention or just a consequence of looking at a different vascular bed compared to the readings from the control day. Mechanisms to address this in the context of a micro-patch with the use of a multichannel integrating probe, a multichannel nonintegrating probe and/or a special assembly are discussed above and illustrated in FIGS. 15-17. Additionally, there is the option to use the inventive micro-patches with embedded microtubules 54 (FIGS. 7 and 10).

Another alternative is provided by the laser Doppler scanning imager. In 1994, I co-authored a study wherein we confirmed the spatial heterogeneity with a laser Doppler scanner. [Wardell K. Braverman T M. Silverman D G. Nilsson G E. Spatial heterogeneity in normal skin perfusion recorded with laser Doppler imaging and flowmetry. Microvascular Research 48(1):26-38, 1994 July]. This demonstrated the value of site-by-site mapping as a means of identifying and potentially overcoming spatial heterogeneity. This is accomplished by rapidly scanning an area by a shifting light that is sequentially directed to successive study sites by a mirror. Although this eliminates some of the problems associated with probe movement, it does not eliminate the problems associated with temporal variability when measurements are successively obtained at neighboring sites. This is because the laser Doppler scanner typically monitors a given site for fractions of a second. Hence, it is less likely to identify pulsations and oscillations in the microcirculation and potentially more likely to be distorted by them. Compromises include rapidly scanning all sites at repeat intervals for a long enough period to overcome the effects of pulsations and oscillations. However, a relatively long interval is required to ensure this. Thus, the laser Doppler scanner mitigates spatial variability at the expense of temporal variability (e.g., beat-to-pulsations with each heart beat as well as oscillations in activity as a component of autonomic regulation of blood vessels.

The micro-patch technology introduced herein is well-suited to monitoring with a laser Doppler scanner; as for the elevated probe assembly (FIG. 16), it does not entail application of the monitoring device to the study site surface and thus is amenable to the alternative micro-applicants discussed above. As illustrated in FIGS. 22-25, the laser Doppler scanner can delineate gradations in blood flow in response to a micro-patch.

Figure 22:
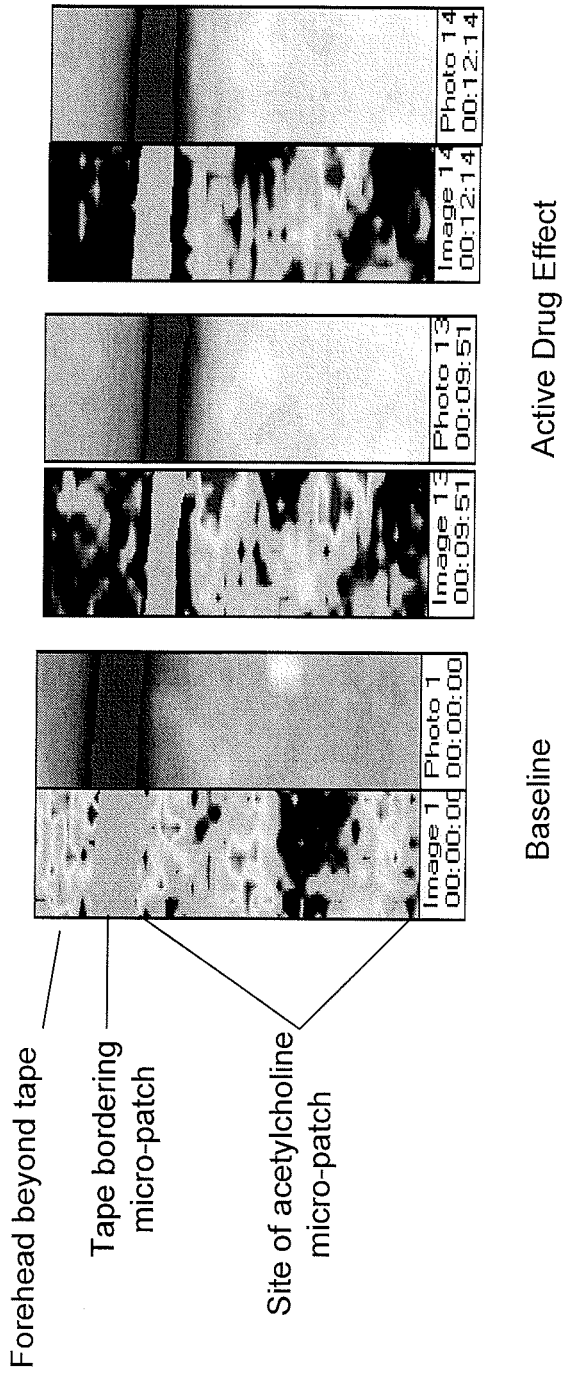
FIG. 22 shows images obtained with laser Doppler scanner depicting relative flow on left and actual picture of site on right before (image 1) and during application of acetylcholine micro-patch to middle of the scanned area of the forehead. Note—the nature of this commercial device is such that gray scale is specific for each image; hence black in one image actually could represent greater flow than gray in another image. Images at 09:51 and 12:14 minutes show lighter areas in the region of drug application (compared to the untreated upper region), indicating increased blood flow as a result of the acetylcholine.
Figure 23:
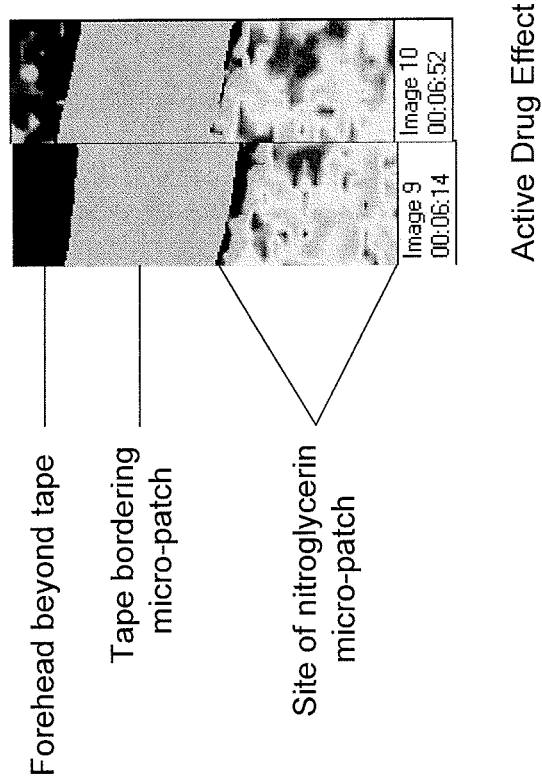
FIG. 23 shows images with laser Doppler scanner in accordance with the present invention 6:14 and 6:52 minutes after application of nitroglycerin micro-patch to the forehead. Increased flow is evident in region of the micro-patch (below the tape).
Figure 24:
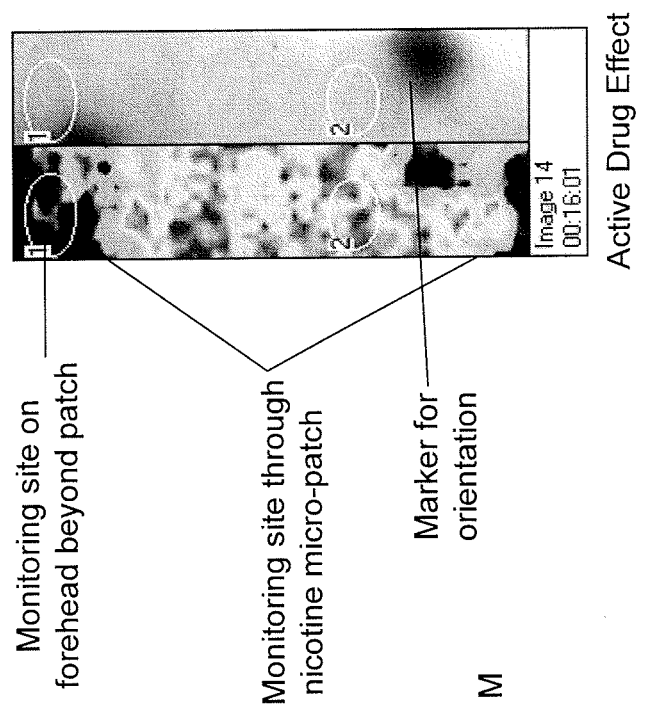
FIG. 24 shows an image and picture obtained with laser Doppler scanner in accordance with the present invention 16:01 minutes after application of nicotine micro-patch in the mid-60% of the scanned area of the forehead. Shades of gray illustrate greatest flow in the area of nicotine micro-patch application.

The increase at the forehead site of the acetylcholine, nitroglycerin and nicotinies micro-patch application in accordance with the present invention are shown with the laser Doppler scanner in FIGS. 22, 23 and 24, respectively. Each figure shows relative flow on left and actual picture of site on right. In each case, images obtained several minutes after micro-patch application show an increase in relative blood flow (color/gray scales) at the site of drug application (below the tape that identifies the border of the micro-patch. (As stated above, it is important to note that the nature of this commercial device is such that gray scale is specific for each image; hence black in one image actually could represent greater flow than gray in another image).

Figure 25:
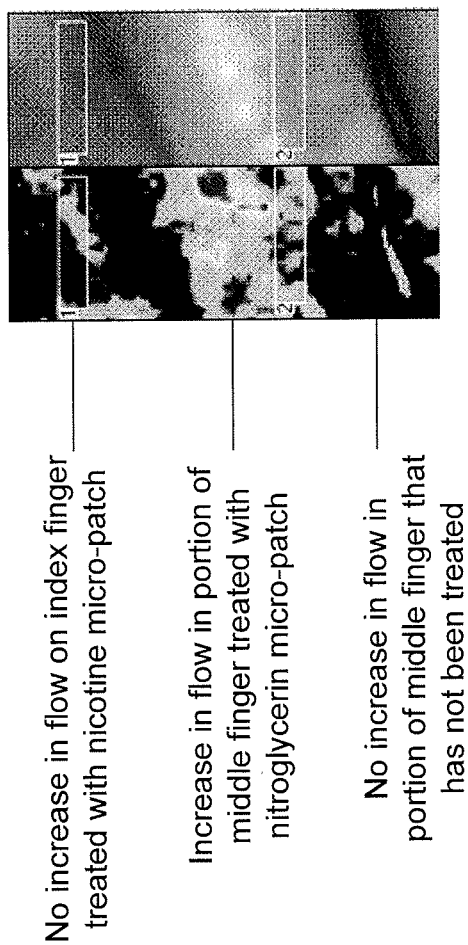
FIG. 25 shows an image and photo obtained with laser Doppler scanner in accordance with the present invention after application of a nicotine micro-patch to index finger and a nitroglycerin micro-patch to middle finger. The fingers have less cholinergic receptors than the forehead. This is supported by the lack of increased flow at the nicotine site. In contrast, flow increased at the nitroglycerin site since the vasodilatory effect of nitroglycerin is independent of said receptors.

An important feature of the present invention is the ability to distinguish responses among different agents at different sites. The laser Doppler images of two fingers in FIG. 25 illustrate this advantage but it should not be construed that such an advantage would not be obtainable with another mechanism of monitoring such as laser Doppler flowmetry probes at each site. Whereas both a nitroglycerin micro-patch (FIG. 23) and a nicotine micro-patch (FIG. 24) caused vasodilation in the forehead, FIG. 25 shows that only the nitroglycerin micro-patch induced vasodilation in the finger. This illustrates the applicability of the present invention to compare different agents at a given region as well as to compare a given agent at different regions—specifically, the data are consistent with the belief that nicotine induces vasodilation at the preganglionic-postganglionic junction of parasympathetic (cholinergic) pathways; these pathways are rich in the forehead and sparse in the finger. Nitroglycerin induces vasodilation independent of the parasympathetic pathways. This disparity is consistent with the reporting by the inventor's team of disparate responses of the finger and forehead after systemic administration of nicotine [Mo C, Stout R G, Shelley K H, Tantawy H, Silverman D G: Acute microcirculatory effects of nicotine in non-smoking volunteers. Anesthesiology 2004; 101:A246.] and phenylephrine [Silverman D G, Stout R G: Distinction between atropine-sensitive control of microvascular and cardiac oscillatory activity. Microvasc Res 63:196-208, 2002]. These studies also provided evidence of sympathetic predominance in the finger and of a relatively greater degree of cholinergic (parasympathetic) activity in the forehead. Such discrimination by a noninvasive micro-patch technique should be extremely helpful in clinical settings.

The aforementioned ability to delineate these distinctions between drugs and locations constitutes a major advantage of the present invention with respect to: comparing agents; comparing sites; identifying which steps in microvascular vasoconstrictive and vasodilatory processes are activated; and assessing the impact of disease, therapies and other interventions.

Limitations of the laser Doppler scanner include:
Higher cost
It requires a more elaborate setup that enables mounting of the laser Doppler scanner above the area of interest
Since available scanners scan each site sequentially, the use of an onsite probe (as opposed to a moving scanner) is preferable if one seeks to delineate the time course of changes or to look at oscillatory changes in blood flow at a given site. However, this also may be accomplished by fixing the laser Doppler scanner at a given test site.
Other aspects of temporal variability discussed above.
Potential options for scanner development to enable simultaneous monitoring of multiple sites, as would be desirable in the context of the inventive micro-patch, include: 1; Single source with a lens (diffractor) that enables delivery and capture of signal from multiple sites at a given session 2. Sends and receives signals via multiple mirrors 3. Multiple light sources that reflect at different sites on a single mirror 4. Multiple beams and multiple mirrors. 5. Incorporating other sites by changing orientation of light source and/or detectors, changing angle of mirror, or moving the mirror(s). These necessitate costly and cumbersome devices.

The limitations imposed by spatial and temporal resolution may be overcome by laser speckle imaging. Here, a single laser light generates a "speckle" as a result of reflection from a heterogeneous surface such as skin. This speckle is blurred in proportion to a dynamic process such as blood flow. The sequential blurring is determined by simultaneous sampling by a multitude of pixels in a standard charged coupled device (CCD) camera array. There is concern, however, that this may not provide the sensitivity to changes in flow afforded by laser Doppler flowmetry, especially if such changes are subtle or compromised by a disease state. Additionally, the speckle pattern may be affected by the consistency of a micro-patch, which might change over the course of time on the skin.

If the laser speckle imager alone cannot effectively document oscillatory activity, then coupling it with a laser Doppler device may overcome this problem. One could set this up so that when one went into the laser Doppler mode, the following would occur:

The efferent link from only a selected number of pixels would be recorded on a CCD; the other pixels on the CCD would virtually be turned off. This would provide a limited output from either a single pixel or a cluster of pixels that would represent a given vascular territory.

The output from the selected pixels would be analyzed by the laser Doppler component to determine frequency shift (degree of shift and amount of shift, i.e., the CMBC and flux components).

This could simply require an output cable. The operator could select the pixel or cluster of pixels that should be used to generate signal for laser Doppler analysis; or this could be automated to select the highest pixel (if that alone would give sufficient amount of light) or the highest cluster of pixels, wherein each highest cluster of pixels wherein each pixel is within a fixed percentage, (e.g., 10% of the highest value).

Unique Applications of Inventive Designs and Methods:

It is contemplated the present invention will be utilized in the following areas:

Dermatological conditions with altered perfusion

Atherosclerosis, coronary artery disease, and peripheral vascular disease

Diabetes with the suspected or documented autonomic neuropathy, vasculopathy and/or end-organ disease Hypertensive, prehypertensive, or potentially prehypertensive patients Patients with eclampsia of pregnancy Patients with migraine and/or menstrual headaches Pain states with an autonomic component Altered autonomic control in patients with congestive heart failure Assessments of altered microvascular autoregulation To document disease progression To test effectiveness of potential therapies To document effectiveness of a prescribed therapy To document unanticipated/undesirable effects of a given therapy. For example, as noted above, testing of a transdermal micro-patch preparation of rofecoxib (Vioxx, Merck Inc) may have identified compromised perfusion at the level of the microvasculature.

To perform integrated assessments of systemic and locally applied medications (and thereby minimize systemic interactions; e.g., to evaluate the potentially harmful systemic interaction when sildenafil (Viagra) and nitroglycerin both are administered systemically. The present invention enable the administration of one of the drugs (e.g., nitroglycerin) in a micro-patch in a singe site, without the risk of dangerous systemic interaction.

Establish dose response curves for individual agents or combination of different agents.

The present disclosure describes the development and initial implementation of the designs and methods to interrogate the local microcirculation during/after noninvasive, noniontophoretic transdermal delivery of vasoactive agents, without concern about significant systemic effects. The clinical utility of the present invention will best be realized after clinical trials with the configurations of agent, agent delivery and monitoring described herein such as:

Carefully regulated production of series of micro-patches with multiple doses of active agents and vehicles Different micro-patch sizes and configuration to determine which leads to most consistent microvascular response as determined by the given monitoring technique Optimization of time course of delivery Monitoring techniques It is well-appreciated that many of the aforementioned conditions are associated with alterations in microvascular function, for example compromised endothelium-dependent and endothelium-independent vasodilation. The present invention offers improved means to characterize such dysfunction and to perform directed assessment, as well as routine screenings, with an easily applied, nonpainful, noninvasive technique. It has been proposed that an ability to document microvascular activity in such a noninvasive manner may revolutionize the assessment of such disorders (Anderson T J: Assessment of endothelial function: research tool or clinical reality? Cardiology Review Endothelial Function Forum CME, July 1999; Anderson T J, Gerhard M D, Meredith I T, et al. Systemic nature of endothelial dysfunction in atherosclerosis. Am J Cardiol 1995; 75:71B; Anderson T J, Overhiser R W, Haber H, Charbonneau F. A comparative study of four anti-hypertensive agents on endothelial function in patients with coronary disease. J Am Coll Cardiol 1998; 31:327A, Abstract #1147-54; Anderson T J, Meredith I T, Yeung A C, et al. The effect of cholesterol-lowering and antioxidant therapy on endothelium-dependent coronary vasomotion. N Engl j Med 1995; 332:488)—the present invention uniquely meets this objective and does so to a degree that previously has not been achieved.

It is further contemplated confirmation of drug delivery in the absence of systemic, remote, or even local changes may be accomplished by a number of techniques known to those skilled in the art. These include: assaying agent levels remaining in micro-patch, tissue surface and within tissue; radioactive or fluorescent labeling to determine amount remaining and/or amount in the tissue. One could establish an index such that the degree of responsiveness is indicative of presence and severity of a disorder. Although it is premature to provide a well-defined index at this time, the data in FIGS. 20 and 21 suggest that an increase in response to transdermal acetylcholine in the forehead of <33% of that in control subject was consistent with advanced diabetic vascular dysfunction. A major benefit of micro-patch technology is for receptor targeting. Even if they target a specific receptor, systemically administered drugs induce multiple effects beyond those at the site. This is especially evident for a drug like nicotine which activates preganglionic to postganglionic fibers throughout the sympathetic and parasympathetic nervous system. It therefore is difficult to discriminate between local and systemic effects. In contrast, only the parasympathetic nervous system has preganglionic to postganglionic synapses at the level of the microvasculature. Hence, micropatch delivery of nicotine can selectively target those structures and enable assessment of their function in health and disease.

While the preferred embodiments have been shown and described, it will be understood that there is no intent to limit the invention by such disclosure, but rather, is intended to cover all modifications and alternate constructions falling within the spirit and scope of the invention.

The invention claimed is:

1. A method for assessing local microvasculature and local microcirculatory vasoreactivity of a patient or research subject by selective noninvasive and nondisturbing monitoring of local microvasculature and local microcirculatory vasoreactivity at an accessible site to noninvasive and nondisturbing trans-surface delivery of a study agent with a known microvascular effect in normal subjects, comprising:

noninvasively delivering a vasoactive study agent to skin of the subject for trans-surface delivery to the microvasculature of the subject, including arterioles, capillaries, venules or to neural structures which selectively innervate microvascular components, in a non-iontophoretic manner to exclusively affect local microvascular vasoreactivity without systemic effects or changes, wherein the step of delivering includes application of a micro-patch containing the study agent to the skin of the subject, the micro-patch containing the study agent selectively affecting the microvasculature at the skin of the subject without potential for confounding influence as a consequence of impact of the study agent on remote sites or on systemic cardiovascular indices, wherein the vasoactive study agent is acetylcholine delivered in an amount equivalent to <0.25 ml of 1% or nitroglycerin delivered at a rate of 0.008 mg/hr;

determining the subject's microvascular responsiveness by measuring changes in microvascular perfusion that are limited to the microvasculature in the area of the skin of the subject beneath the micro-patch;

ensuring that drug delivery does not induce alterations in measurements by delivery to remote sites or by systemic effects wherein this is accomplished by real-time monitoring of heart rate, blood pressure, or flow at other sites or such monitoring has been used to establish parameters for delivery of said agent below those which might induce said confounding changes; and assessing local microvasculature and local microcirculatory vasoreactivity based upon the steps of delivering, determining, and ensuring.

2. The method according to claim 1, wherein the micro-patch includes a transparent backing, the study agent to be delivered, and a protective cover member.

3. The method according to claim 1, wherein the micro-patch includes a transparent backing, a carrier vehicle in which the study agent is encapsulated and a protective cover member.

4. The method according to claim 1, wherein the micro-patch includes mini-projections.

5. The method according to claim 1, wherein the micro-patch includes reverse projections that extend into the micro-patch to open up channels for delivery of the study agent.

6. The method according to claim 1, further including studying microcirculation at multiple sites.

7. The method according to claim 6, wherein the probe is laser Doppler flowmetry probe.

8. The method according to claim 6, wherein the probe is mounted upon a probe holder for selective movement of the probe relative to the probe holder.

9. The method according to claim 1, wherein the micro-patch has a diameter of approximately 0.25 cm to approximately 2.5 cm.

10. The method according to claim 1, wherein the micro-patch has a delay mechanism for delivery of the study agent.

11. The method according to claim 1, wherein the step of delivering a study agent is regulated to facilitate attainment of baseline readings before delivery of an effective amount of the study agent.

12. The method according to claim 1, wherein study agents with differing modes of action are administered at the same micro-patch site.

13. The method according to claim 1, wherein two study agents are applied and monitored concurrently.

14. The method according to claim 1, wherein measurements during a plateau phase are obtained within 5-20 minutes after delivery of the study agent.

15. The method according to claim 1, wherein changes are detected within one minute of drug application.

16. The method according claim 1, wherein the step of assessing includes assessing magnitude of change in mean, systolic, diastolic and systolic minus diastolic values of individual beats, and/or assessing rate of rise or decline of mean, systolic or diastolic values of individual beats, and/or assessing oscillatory patterns of multiple beats.

17. A method for determining a drug's otherwise uncertain effect on the arterioles, capillaries or venules comprising the microvasculature by selective noninvasive and nondisturbing monitoring of microvascular response to noninvasive and nondisturbing trans-surface delivery of the drug in an individual in whom a status of the systemic microvasculature already is known, comprising:

noninvasively delivering a study agent to skin of a subject for trans-surface delivery to the microvasculature of the subject, the microvasculature including arterioles, capillaries, venules or to neural structures which selectively innervate microvascular components, in a non-iontophoretic manner to exclusively affect local microvascular vasoreactivity without systemic effects or changes, wherein the step of delivering includes application of a micro-patch containing the study agent to the skin of the subject, the micro-patch containing the study agent potentially affecting the microvasculature at the skin of the subject without potential for confounding influence as a consequence of regional spread or systemic uptake of the study agent, wherein the vasoactive study agent is acetylcholine delivered in an amount equivalent to <0.25 ml of 1% or nitroglycerin delivered at a rate of 0.008 mg/hr, determining a microvascular responsiveness of a subject to the study agent by measuring changes in microvascular perfusion that are limited to the microvasculature in the area of the skin of the subject beneath the micro-patch, ensuring that delivery of the study agent does not induce alterations in measurements by spread to remote sites or by systemic effects wherein this is accomplished by real-time monitoring of heart rate, blood pressure, or flow at other sites or such monitoring has been used to establish parameters for delivery of the study agent below those which might induce confounding changes; and assessing local microvasculature and local microcirculatory vasoreactivity based upon the steps of delivering, determining, and ensuring.

18. The method according claim 17, wherein, for a given study agent, dosing parameters are determined with respect to a rate of delivery and a duration of delivery to provide a desired degree of response in healthy subjects while ensuring lack of confounding effects due to an effect on large vessels.

19. The method according to claim 17, further including the step of obtaining a baseline reading prior to delivery of the study agent with a monitor sensitive to microvascular function or microvascular flow.

20. The method according to claim 19, further including the step of monitoring continuously until attainment of plateau phase for up to approximately one hour after onset of effect, wherein monitoring confirms a lack of potentially confounding impact on the study site as a consequence of changes in major vessels, noncontiguous sites, or systemic cardiovascular parameters.

21. The method according claim 1, further including the step of identify function and status of the parasympathetic nervous system with nicotine.

22. The method according to claim 1, further including the step of assessing impact of a transient or persistent condition that may selectively affect a particular component of the microvasculature.

23. The method according to claim 21, wherein the component of the microvasculature is the nicotinic receptor of the parasympathetic nervous system that is located at the level of the microvasculature.

24. The method according to claim 1, wherein a condition being assessed similarly impacts accessible and inaccessible microvasculature.

25. The method according to claim 1, wherein a common microvascular receptor that is being assessed in a periphery as an indicator of systemic vasculature is on the microvascular endothelium.

26. The method according to claim 25, wherein the common microvascular receptor is a nicotinic receptor that is located at the microvasculature of the study site as well as the inaccessible vasculature.

* * * * *